US007629003B2

(12) United States Patent
Pisano et al.

(10) Patent No.: US 7,629,003 B2
(45) Date of Patent: Dec. 8, 2009

(54) ESTERS OF L-CARNITINE OF ALKANOYL L-CARNITINES USEFUL AS CATIONIC LIPIDS FOR THE INTRACELLULAR DELIVERY OF PHARMACOLOGICALLY ACTIVE COMPOUNDS

(75) Inventors: Claudio Pisano, Aprilia (IT); Maria Ornella Tinti, Rome (IT); Mosé Santaniello, Nettuno (IT); Luciana Critelli, Pomezia (IT); Giovanni Salvatori, Rome (IT)

(73) Assignee: Sigma-Tau Farmaceutiche Riunite S.p.A., Rome (IT)

( * ) Notice: Subject to any disclaimer, the term of this patent is extended or adjusted under 35 U.S.C. 154(b) by 325 days.

(21) Appl. No.: 10/624,645

(22) Filed: Jul. 23, 2003

(65) Prior Publication Data
US 2005/0079209 A1    Apr. 14, 2005

Related U.S. Application Data

(62) Division of application No. 09/958,328, filed on Oct. 9, 2001, now Pat. No. 6,797,281.

(51) Int. Cl.
*A61K 9/127* (2006.01)
(52) U.S. Cl. ..................................... 424/450
(58) Field of Classification Search ................ 424/450, 424/1.21, 9.321, 9.51, 417
See application file for complete search history.

(56) References Cited

U.S. PATENT DOCUMENTS

| 5,008,288 A * | 4/1991 | Stracher et al. ............. 514/535 |
| 5,552,156 A * | 9/1996 | Burke ......................... 424/450 |
| 5,653,996 A * | 8/1997 | Hsu .......................... 424/450 |
| 5,811,406 A | 9/1998 | Szoka, Jr. et al. |
| 6,008,202 A * | 12/1999 | Huang et al. ................... 514/44 |
| 6,056,973 A * | 5/2000 | Allen et al. ................. 424/450 |
| 6,171,614 B1 * | 1/2001 | Chaikof et al. .............. 424/450 |

FOREIGN PATENT DOCUMENTS

| EP | 0 279 887 A2 | 8/1988 |
| EP | 0 559 625 A2 | 9/1993 |
| WO | WO 96/39193 | 12/1996 |
| WO | WO 99/57094 | 11/1999 |

OTHER PUBLICATIONS

Wang, Jinkang et al; Synthesis and Characterization of Long Chain Alkyl Acyl Carnitine Ester. Potentially Biodegradable Cationic Lipids for Use In Gene Delivery; J. Med. Chem. (1998), 41(13), 2207-2215, cited in the application p. 2208.

* cited by examiner

*Primary Examiner*—Gollamudi S Kishore
(74) *Attorney, Agent, or Firm*—Lucas & Mercanti, LLP

(57) ABSTRACT

Esters of L-carnitine and alkanoyl L-carnitines are described which can be used as cationic lipids for the intracellular delivery of pharmacologically active compounds. New esters of L-carnitine and alkanoyl L-carnitines of formula (I) are also disclosed wherein the R groups are as defined in the description.

48 Claims, 3 Drawing Sheets

|  | 30 min. | 4 hours | % | 4 hours |
|---|---|---|---|---|
| dna | 1990,567 | 19424,67 | 0 | 0 |
| 772MLV 79 | 1858214 | 13123082 | 67 | 71 |
| 772MLV 80 | 2219863 | 15360769 | 80 | 83 |
| dotap 24/9/98 | 2771950 | 18474757 | 100 | 100 |
| dotap 29/9/98 | 2535507 | 17090549 | 91 | 93 |

Preliminary data of tissue contents (lung) of ST1481-liposomes delivered in i.v. injected mice (q4dx4)

Mice were sacrificed 24 h after the last treatment. Values represent the pooled lung samples expressed as means +/-SE.

ESTERS OF L-CARNITINE OF ALKANOYL L-CARNITINES USEFUL AS CATIONIC LIPIDS FOR THE INTRACELLULAR DELIVERY OF PHARMACOLOGICALLY ACTIVE COMPOUNDS

This application is a division of application Ser. No. 09/958,328, filed Oct. 9, 2001, now U.S. Pat. No. 6,797,281.

The invention described herein relates to a class of new esters of L-carnitine and acyl L-carnitines and their use as cationic lipids suitable for favouring the intracellular delivery of pharmacologically active compounds, facilitating their transmembrane transport, or for promoting their interaction with specific cell membrane sites (receptors).

The invention described herein also relates to further known esters of L-carnitine and acyl L-carnitines, useful for the same purposes as the above-mentioned new compounds.

What is meant here by the term "intracellular delivery" is cellular transfection with polynucleotides or plasmids of natural origin or modified, endowed with therapeutic activity (gene delivery) or the introduction of drugs or immunogenic peptides into the cells.

Many of the pharmacologically active substances, such as, for instance, polypeptides and proteins or drugs in general need to penetrate into the cells to exert their effects by influencing cell functions at subcellular or molecular level. For these molecules the cell membrane constitutes a selectively impermeable barrier. The cell membrane, in fact, performs a protective function, preventing the entry of potentially toxic substances, but also the passage of compounds with therapeutic activity. The complex composition of the cell membrane includes phospholipids, glycolipids and proteins; its function is influenced by cytoplasmatic components such as $Ca^{++}$ and other ions, ATP, microfilaments, microtubules, enzymes and proteins that bind $Ca^{++}$. The interaction between the structural and cytoplasmatic components of the cells and the response to external signals are responsible for the selectivity shown by and among the various different cell types. The barrier effect of the membranes can be overcome by combining substances in complexes with lipid formulations that reproduce the composition of naturally occurring membrane lipids. These lipids are capable of fusing with the membranes and of releasing the substances combined with them into the cells. The lipid complexes are capable not only of facilitating intracellular transfer by means of fusion with the membranes, but can also diminish the charge repulsion between the membrane and the molecule that has to penetrate into the cell. Amphipathic lipids, such as membrane phospholipids, form lipid vesicles or liposomes in the aqueous systems.

Liposomes are vesicles in which an aqueous volume is entirely enclosed by one or more membranes composed of lipid molecules, usually phospholipids. Phospholipids, which consist in a hydrophilic head and a pair of carbon chains (hydrophobic tail), are the main components of biological membranes. In aqueous solution the hydrophobic tails autoassociate to exclude water, while the hydrophilic heads interact with the medium, spontaneously forming populations of vesicles of varying diameters. The lipids are generally zwitterionic, neutral or anionic. These vesicles can be used as carriers of drugs, small molecules, proteins, nucleotides and plasmids.

Over recent years, the cationic liposomes, a class of positively charged vesicles prepared from synthetic lipids, have been extensively used for the transfer of genetic material into the cells. The negative charge of DNA can interact with the positive charges of the cationic lipids, forming a stable DNA-liposome complex. The simplicity and versatility of this technology have made liposomes an important vehicle for the delivery of genes for gene therapy in human subjects. Currently, most of the vectors used for gene therapy and approved by the NIH Recombinant Advisory Committee include viral and synthetic systems.

Viral infection involves a series of complex mechanisms in order to be able to attack a specific cell and carry the DNA into the nucleus. The rationale for the use of viral vectors for gene therapy is based on the possibility of replacing the viral genes with genes that code for a therapeutic function, without eliminating the ability of the viral particle to infect the cells. The limitations of viral therapy have to do with those viral elements that may be immunogenic, cytopathic and recombinogenic.

Great hopes are placed in the use of cationic lipids for gene therapy. These vectors possess great potential compared with those of biological origin, since they are much safer, less toxic and are also capable of incorporating genes of large size. As compared with biological-type vectors, however, they have a low intracellular gene transcription yield. It should be borne in mind, however, that the use of such transfection systems is in an initial stage of research. Cationic lipids play a very important role in the formation of the DNA-lipid complex, in cell-complex interaction, in fusion with the membrane, in DNA release inside the cell and in transcription.

There are important examples of in-vivo applications of cationic liposomes. The first clinical trial on gene therapy was conducted by introducing an expression vector containing the human liposome-complexed HLA-B7 gene for the treatment of melanoma. Another important application relates to the treatment of pulmonary cystic fibrosis by means of the administration via the pulmonary route or as a nasal spray of the liposome-complexed expression vector SV-40C-FTR. Other clinical trials involving the use of liposomes in gene therapy for cancer are currently in progress.

Four constituent elements are generally identified in the structure of cationic lipids: the positively charged cationic head, the spacer, the anchor lipid and the linker bond.

The cationic head is responsible for the interactions between cationic liposomes and DNA, between the DNA-liposome complex and the cell membrane and the other components of the cell. It consists of mono- or polycationic groups (depending on the number of charges) that can be variably substituted.

The spacer is the part of the molecule that separates the cationic head from the hydrophobic tail and is involved in ensuring optimal contact between the cationic head and the negative charges of the DNA phosphates.

The anchor lipid is the non-polar hydrocarbon part of the molecule and determines the physical properties of the double lipid layer, such as its rigidity and rate of exchange with membrane lipids.

What is meant by "linker bond" is the bond between the hydrocarbon chains and the rest of the molecule. This bond determines the chemical stability and biodegradability of the cationic lipids.

In recent years the use of liposomes has steadily increased in the cosmetics sector. The success of liposomes in this field is due to the fact that these compounds are very well tolerated by the skin. They are used both as vehicles for active ingredients and as compounds favouring the absorption of the latter.

The scientific and patent literature is rich in references to the preparation and use of liposomes; there are, however, very few references describing the use of carnitine derivatives useful for gene delivery, whereas for drug delivery no documents are available dealing with known techniques for the preparation of compounds remotely resembling those according to the invention described herein.

Patent application EP 0 279 887 describes the use of a derivative of carnitine, i.e. phosphatidyl carnitine, optionally in mixtures with other phospholipids and lipids (cholesterol, phosphatidyl choline, phosphatidyl serine), for the preparation of liposomes.

In the example provided regarding the preparation of liposomes, liposomes of phosphatidyl carnitine are produced which incorporate propranolol, a drug known to be active as an antihypertensive, anti-angina and antiarrhythmia agent. The carnitine derivative is used here on account of the pronounced myocardial tropism of carnitine. This tropism makes it possible to avoid the liposomes being metabolised by the liver, rather than reaching the desired target site.

The presence of phosphatidyl carnitine also makes it possible to administer the liposomes orally, since they are resistant to intestinal lipases.

In J. Med. Chem. 1998 Jun. 18; 41(13):2207-15, a number of esters of L-carnitine useful for gene delivery are described, but they are not described or proposed as useful agents for drug delivery.

WO 96/39193 describes novel targeting drug agents that are targeted for entry into the mitochondria via the carnitine-acylcarnitine traslocase system, but does not suggest them as useful agent for preparing liposomes.

EP 559 625 B1 describes a number of esters of L-carnitine and acyl L-carnitines endowed with selective gastrointestinal tract muscle-relaxing activity.

In recent years molecular biologists have identified numerous defects at the chromosomal level that cause hereditary diseases in human subjects.

An important sector of modern medicine is concerned with the treatment of these hereditary genetic-based diseases by means of the use of gene therapy protocols.

As already mentioned, cationic liposomes are extensively used for the intracellular delivery of pharmacologically active compounds, facilitating transmembrane transport or promoting their interaction with specific cell membrane sites (receptors).

These vectors have great potential as compared to those of biological origin, since they are much safer, less toxic and are also capable of incorporating genes of large size. As compared to biological-type vectors, however, they have a low intracellular gene transcription yield.

Moreover, gene transfer mediated by conventional cationic lipids requires that plasmid DNA and cationic lipids be kept separate, and that their mixing be effected immediately before gene transfer.

Attempts to stabilise these polynucleotide complexes have so far failed to yield encouraging results; in fact, they remain stable only for a short period.

In the field of gene therapy or gene delivery and drug delivery, there is therefore a strongly perceived need for stable, reproducible site-specific systems which are also active after a suitable period of time.

It has now been found that a class of cationic lipids powerfully active in promoting the intracellular delivery of pharmacologically active compounds comprises the new esters of L-carnitine and acyl L-carnitines.

These new compounds are stable and highly selective because they are site-specific in reaching the target organ.

This characteristic makes them particularly useful for the transport of active compounds directly to the site where they can exert their pharmacological activity.

Figure 1:
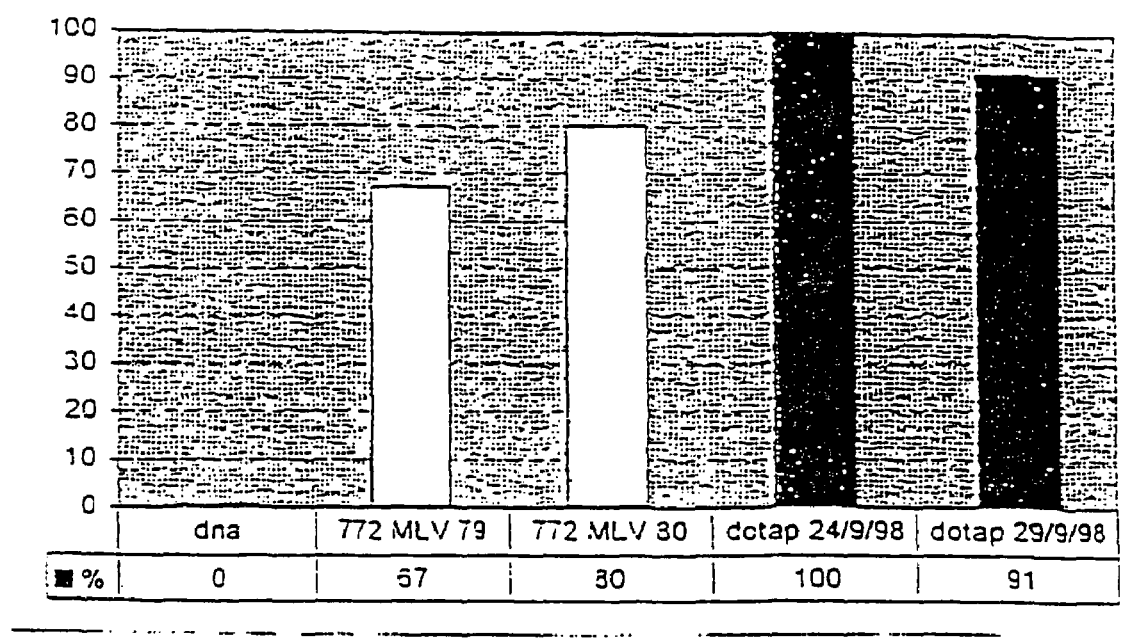
FIG. 1 shows the plasmid DNA transfection efficiency of the ST 772 liposome in HeLa cells (densitometric analysis).

The compounds according to the invention described herein are compounds with general formula (I):

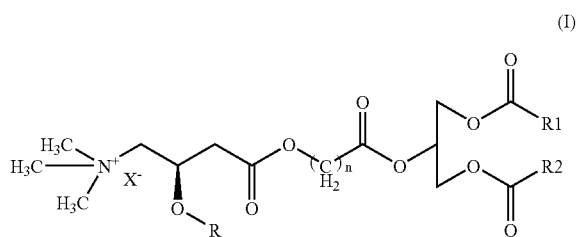

where:

n is an integer from 1 to 3;

R is hydrogen or alkanoyl, straight or branched, with 2-6 carbon atoms;

$R_1$ and $R_2$, which may be the same or different, represent a saturated or unsaturated straight acyl chain, with 3-20 carbon atoms; and $X^-$ is the anion of a pharmacologically acceptable acid.

Examples of R are acetyl, propionyl, butyryl, valeryl and isovaleryl.

Examples of $R_1$ and $R_2$ are hexanoyl, undecanoyl, myristoyl, palmitoyl or oleoyl.

Preferred examples of compounds according to the invention are:

ester of L-carnitine bromide with 2-hydroxyacetyl-1,3-dipalmitoyl glycerol (ST 770);

ester of acetyl L-carnitine bromide with 2-hydroxyacetyl-1,3-dipalmitoyl glycerol (ST 771);

ester of propionyl L-carnitine bromide with 2-hydroxyacetyl-1,3-dipalmitoyl glycerol (ST 772);

ester of isobutyryl L-carnitine bromide with 2-hydroxyacetyl-1,3 dipalmitoyl glycerol (ST 773);

ester of isovaleryl L-carnitine bromide with 2-hydroxyacetyl-1,3-dipalmitoyl glycerol (ST 774);

ester of L-carnitine bromide with 1,3-dihexanoyl-2-hydroxycetyl glycerol (ST 810);

ester of acetyl L-carnitine bromide with 1,3-dihexanoyl-2-hydroxyacetyl glycerol (ST 809).

ester of propionyl L-carnitine bromide with 1,3-dihexanoyl-2-hydroxyacetyl glycerol (ST 808).

What is meant by an anion of a pharmacologically acceptable acid is any anion of an acid that does not give rise to unwanted toxic or side effects.

These acids are well known to pharmacologists and to experts in pharmaceutical technology.

Examples of these anions, though not exclusively the ones listed, are: chloride; bromide; iodide; aspartate; acid aspartate; citrate; acid citrate; tartrate; acid tartrate; phosphate;

acid phosphate; fumarate; acid fumarate; glycerophosphate; glucose phosphate; lactate; maleate; acid maleate; mucate; orotate; oxalate; acid oxalate; sulphate; acid sulphate; trichloroacetate; trifluoroacetate; methane sulphonate; pamoate and acid pamoate.

Compounds of formula (I), in the form of liposomes, are agents useful both for the delivery of naturally occurring or modified plasmids or nucleotides useful in gene therapy, or which code for a peptide or protein useful as a vaccine, and for the general delivery of drugs, such as, for instance, anticancer drugs, antiviral agents, antibacterial agents, antifungals, antiprotozoans, drugs useful for the therapy of cardiovascular system diseases, or immunogenic peptides and other drugs useful in therapy.

The liposomes containing the compound of formula (I) are prepared by means of conventional techniques, well-known to the person having ordinary skill in the art; see for example Allen T. M. Drugs 56, 747-56 (1998). The liposomes according to the present invention may be prepared also by using other components well-known in the practice of liposome technology. In one embodiment of the present invention, the liposomes may contain helper lipids, a term which is well understood in this art. Examples of helper lipids are cholesterol, 1-palmitoyl-2-oleoyl phosphatidyl choline or dioleyl phosphatidyl choline.

The liposomes according to the present invention are suitably presented as compositions. In the embodiment pertaining to delivery of pharmacologically active compounds, the compositions are understood as pharmaceutical ones, optionally comprising pharmaceutically acceptable vehicles and/or excipients.

Compounds of formula (I), in the form of liposomes, may also be useful in the preparation of cosmetic compositions, both comprising the liposome per se as cosmetic active agent and for the delivery of substances with cosmetic activity, such as, for instance, hydrating agents, nutrients, substances for facial cleansing, anti-wrinkle agents, anticellulitis agents and anti-stretch-mark agents.

Liposomes comprising the compounds of formula (I) can be administered orally or parenterally, intravenously, intramuscularly, subcutaneously, transdermally, or in the form of nasal or mouth sprays.

The invention described herein also relates to additional cationic lipids with general formula (II), already known for a different use (EP 559 625 mentioned above).

According to the present invention, the compounds of formula (II) are esters of L-carnitine, useful for the preparation of liposomes which possess potent activity in drug delivery and present characteristics of stability and selectivity in reaching the target organ comparable to those of the compounds of formula (I) described above. The same advantageous properties are applicable in case of cosmetics.

These compounds have the general formula (II):

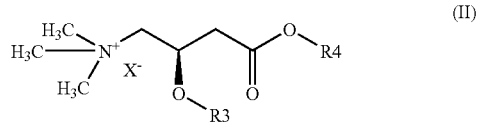

(II)

where:

$R_3$ is a saturated or unsaturated, straight or branched acyl chain, with 4-26 carbon atoms;

$R_4$ is a saturated or unsaturated, straight or branched alkyl chain, with 4-26 carbon atoms; and $X^-$ is the anion of a pharmacologically acceptable acid.

Preferred examples of $R_3$ are nonanoyl, dodecanoyl, myristoyl, palmitoyl, stearoyl or oleoyl.

Preferred examples of $R_4$ are nonyl, undecyl, tetradecyl, hexadecyl or oleyl.

Examples of specific compounds of formula (II), according to the invention described herein are:

palmitoyl L-carnitine chloride undecyl ester (ST 983);
stearoyl L-carnitine chloride undecyl ester (ST 1055);
stearoyl L-carnitine chloride tetradecyl ester (ST 1351);
palmitoyl L-carnitine chloride tetradecyl ester (ST 1379);
myristoyl L-carnitine chloride tetradecyl ester (ST 1380);
palmitoyl L-carnitine bromide hexadecyl ester (ST 1390);
oleyl L-carnitine chloride oleyl ester (ST 1392).

A number of compounds of formula (II), namely ST 1380, ST 1390 and ST 1392, are known and described in the above-cited J. Med. Chem. 1998 Jun. 18; 41(13):2207-15, as useful agents for the preparation of liposomes for cellular transfection endowed with therapeutic activity, but have never been described as useful agents for the preparation of liposomes for drug delivery.

The skilled person with average experience in the field of pharmaceutical formulations is well aware of the difficulties encountered in preparing liposome-drug complexes; in fact, it is impossible to establish a priori whether a liposome which is useful for gene delivery can be used for drug delivery owing to the numerous problems which must be overcome to obtain a liposome capable of complexing a drug and which will deliver it preferentially to the organ where it has to exert its curative activity.

Compounds of formula (II), in the form of liposomes, are useful agents for the delivery of drugs, such as, for instance, anticancer, antiangiogenic, antiviral, antibacterial, antifungal, antiprotozoan agents, or drugs useful for the therapy of cardiovascular diseases, or immunogenic peptides, and other drugs useful in therapy.

Compounds of formula (II), in the form of liposomes, are also useful in the preparation of cosmetic compositions as cosmetic agents per se or for the delivery of substances with cosmetic activity, such as, for instance, hydrating agents, nutrients, facial cleansing agents, and anti-wrinkle, anticellulitis and anti-stretch-mark agents.

Said liposomes may optionally comprise helper lipids as in the case of the liposomes comprising compounds of formula (II).

Liposomes comprising compounds of formula (II) can be administered orally or parenterally, intravenously, intramuscularly, subcutaneously, transdermally, or in the form of nasal or mouth sprays.

The invention described herein also relates to additional cationic lipids with general formula (III), already known for a different use (EP 559 625 mentioned above).

According to the present invention, the compounds of formula (III) are esters of L-carnitine, useful for the preparation of liposomes which possess potent activity in promoting drug delivery and present characteristics of stability and selectivity in reaching the target organ comparable to those of the compounds of formula (I) described above.

These compounds have the general formula (III):

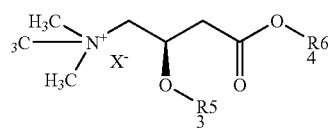

where:

R₅ is a saturated or unsaturated, straight or branched acyl chain, with 4-26 carbon atoms;

R₆ is a saturated or unsaturated, straight or branched alkyl chain, with 4-26 carbon atoms; and X⁻ is the anion of a pharmacologically acceptable acid;

with the proviso that:

when $R_5$ is stearoyl, $R_6$ is not stearyl, when $R_5$ is oleoyl, $R_6$ is not stearyl, when $R_5$ is palmitoyl, $R_6$ is not palmityl, when $R_5$ is myristoyl, $R_6$ is not myristyl, when $R_5$ is lauroyl, $R_6$ is not lauryl, when $R_5$ is oleoyl, $R_6$ is not oleyl.

The disclaimed compounds in the form of liposomes are disclosed in J. Med. Chem. 1988, 41, 2207-2215 exclusively for gene delivery.

Preferred examples of $R_5$ are nonanoyl, dodecanoyl, myristoyl, palmitoyl, stearoyl or oleoyl.

Preferred examples of $R_6$ are nonyl, undecyl, tetradecyl, hexadecyl or oleyl.

Preferred examples of compounds of formula (III) according to the invention described herein are:

palmitoyl L-carnitine chloride undecyl ester (ST 983);
stearoyl L-carnitine chloride undecyl ester (ST 1055);
stearoyl L-carnitine chloride tetradecyl ester (ST 1351);
palmitoyl L-carnitine chloride tetradecyl ester (ST 1379).

Compounds of formula (III) are useful agents for the delivery of naturally occurring or modified plasmids or nucleotides useful in gene therapy or which code for a peptide or protein useful as a vaccine.

Compounds of formula (III) can be administered orally or parenterally, intravenously, intramuscularly, subcutaneously, transdermally, or in the form of nasal or mouth sprays.

The procedure for the preparation of compounds of formula (I) according to the invention is represented in the following reaction diagram, being intended that this diagram applies to the whole general formula (I). The skilled person can easily obtain all the groups meant in R, R₁ and R₂, since all the necessary regents are commercially available or disclosed in literature and reaction conditions are generally applicable to the whole scope of the present invention any modification, if necessary is normally achieved within the general common knowledge.

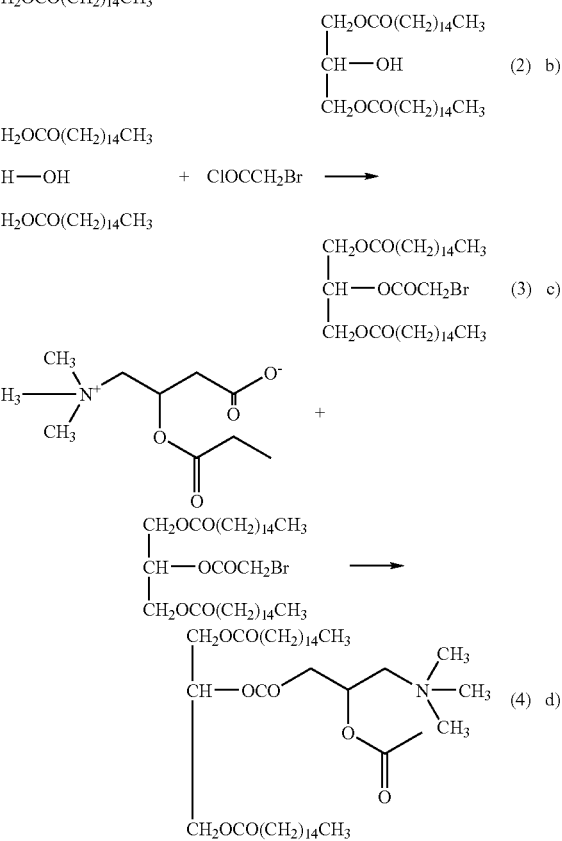

With reference to the above reaction diagram 1, the preparation of compounds of formula (I) according to the invention is illustrated here below.

EXAMPLE 1

Preparation of the Ester of Propionyl L-Carnitine Bromide with 2-Hydroxy Acetyl 1,3 Dipalmitoyl Glycerol (ST 772)

a) Preparation of 1,3-dihydroxypropan-2-one 1,3-dipalmitate (1)

Dihydroxyacetone (7 g; 0.078 mol) was dissolved in 300 mL of anhydrous chloroform at 0° C. (external temperature) under anhydrous nitrogen flow.

To the solution thus obtained palmitoyl chloride (44 g; 0.16 mol) and anhydrous pyridine (15 mL) were added dropwise.

The resulting mixture, the temperature of which was brought up to ambient temperature, was maintained under stirring for 24 hours.

The mixture was then extracted in the following order: with 300 mL of an aqueous solution of 0.5% hydrochloric acid, 300 mL of an aqueous solution of 5% sodium bicarbonate and lastly with 300 mL of water.

The separated organic phase was dehydrated on anhydrous sodium sulphate, filtered on a cellulose filter and concentrated to dryness, obtaining crude product (1).

Pure product (1) was obtained by crystallisation from 500 mL of ethyl alcohol.

30.4 g of product (1) were obtained.
Yield: 73%
m.p.=80-81° C.
H$^1$NMR (CDCl$_3$): 0.9 (6H, t, C$\underline{H_3}$CH$_2$—); 1.3 (48H, m, (CH$_2$)$_{n=24}$); 1.55 (4H, m, —OCOC$\underline{H_2}$C$\underline{H_2}$—); 2.4 (4H, t, —OCOC$\underline{H_2}$—); 4.7 (4H, s, —OCC$\underline{H_2}$—).

b) Preparation of 1,2,3-trihydroxyropane-1,3-dipalmitate (2)

Water (7.5 mL) was added slowly to product (1) (5 g, 9 mmol), dissolved in tetrahydrofuran (125 mL) and toluene (25 mL) under stirring.

The temperature of the milky white suspension obtained was brought to 5° C. (external temperature) and sodium borohydride (500 mg; 13 mmol) was added in small portions. The suspension was maintained under stirring for 30 minutes at 5° C.

Glacial acetic acid was then added slowly until the effervescence produced by the decomposition of the excess sodium borohydride ceased, finally obtaining a solution.

Chloroform (100 mL) was added to the solution, obtaining the formation of a biphasic system.

The lower organic phase consisting of CHCl$_3$ was separated, being extracted in the following order: with water (25 mL), sodium bicarbonate (25 mL of 10% aqueous solution) and water (25 mL).

The organic solution containing (2) was dehydrated on sodium sulphate, filtered and concentrated to dryness, obtaining a wax-like product.

Product (2) was obtained by acetone crystallisation of the wax-like crude product. 4.8 g of product (2) were obtained.
Yield: 94%.
m.p.=71-72° C.
H$^1$NMR(CDCl$_3$): 0.9 (6H, t, C$\underline{H_3}$CH$_2$—); 1.3 (48H, m, (CH$_2$)$_{n=24}$); 1.55 (4H, m, —OCOC$\underline{H_2}$C$\underline{H_2}$—); 2.4 (4H, t, —OCOC$\underline{H_2}$—); 4.2 (5H, m, —C$\underline{H}$C$\underline{H_2}$O—).

c) Preparation of 1,3-dipalmitoyl-2-bromoacetyl glycerol (3)

Product (2) (2.5 g; 4.4 mmol) was solubilised in anhydrous chloroform (50 mL) under stirring and at 0° C. (external temperature).

To the solution thus obtained were slowly added pyridine (0.42 ml) and dropwise 3 ml of a chloroform solution containing bromo-acetylchloride (0.43 mL; 5.2 mmol).

The reaction mixture was held for 30 minutes at 0° C. (external temperature) and for 30 minutes at ambient temperature.

The reaction mixture was then treated in the following order with: an aqueous solution of 1% hydrochloric acid (50 mL approx.), an aqueous solution of 5% sodium bicarbonate (50 mL approx.) and water.

Product (3) was purified by acetone crystallisation, after dehydrating the reaction mixture (with sodium sulphate) and concentrating to dryness.

2.5 g of product (3) were obtained.
Yield: 89%.
m.p.=46-47° C.
H$^1$NMR (CDCl$_3$): 0.9 (6H, t, C$\underline{H_3}$CH$_2$—); 1.3 (48H, m, (CH$_2$)$_{n=24}$); 1.55 (4H, m, —OCOC$\underline{H_2}$C$\underline{H_2}$—); 2.4 (4H, t, —OCOC$\underline{H_2}$—); 3.9 (2H, s, —OC$\underline{H_2}$COO—) 4.2-4.4 (5H, m, —CHC$\underline{H_2}$O—); 5.25 (1H, m, C$\underline{H}$CH$_2$O—).

d) Preparation of the Ester L-Propionyl Carnitine Bromide with 2-hydroxyacetyl-1,3-dipalmitoylglycerol (4)

L-propionyl carnitine inner salt (0.95 g, 4.4 mmol) previously vacuum dried at 40° C. was suspended in anhydrous dimethylformamide (20 mL approx.).

Product (3) (3 g, 4.7 mmol) was added to the suspension in small portions. The suspension was heated slowly to 38° C. and held in these conditions until a solution was obtained.

After 10 minutes the solution was brought to 0° C. for 30 minutes. A precipitate was obtained, which was filtered and washed with ethyl ether and dissolved in chloroform (100 mL). The opalescent solution obtained (30 mL) was filtered on celite and concentrated. To this latter solution was added hexane (100 mL), and the precipitate of product (4) obtained was filtered and vacuum dried at 35° C.

3.19 g of the titre compound were obtained.
Yield: 80%.
m.p.=127-128° C.
$[\alpha]^{25}_D$=−3.9 (C=1% chloroform)
Elemental analysis of C$_{47}$H$_{88}$BrNO$_{10}$

|  | C % | H % | N % | Br % |
|---|---|---|---|---|
| Calculated | 62.23 | 9.78 | 1.54 | 8.81 |
| Found | 62.73 | 10.15 | 0.79 | 8.77 |

H$^1$ NMR (CDCl$_3$):0.9-0.95 (6H, t, C$\underline{H_3}$CH$_2$CH$_2$—); 1.1-1.2 (3H, t, C$\underline{H_3}$CH$_2$CO); 1.2-1.4 (24H, m, CH$_2$n=24); 1.5-1.6 (4H, m, —OCC$\underline{H_2}$C$\underline{H_2}$—); 2.3-2.4 (4H, t, —OCC$\underline{H_2}$CH$_2$—); 2.4-2.45 (4H, d.d., —CHCH$_2$O—); 2.95 (2H, d, —C$\underline{H_2}$COOCH$_2$COO—); 3.5 (9H, s, N(C$\underline{H_3}$)$_3$); 4.2 (4H, m, —C$\underline{H_2}$OCOCH$_2$—); 4.35 (2H, m, —C$\underline{H_2}$N—); 4.65 (2H, d, d, —OC$\underline{H_2}$CO—); 5.25 (1H, m, —OC$\underline{H_2}$CHCH$_2$O—); 5.75 (1H, m, —C$\underline{H}$CH$_2$N—).

EXAMPLES 2-7

The following compounds were prepared in the same way as in the preceding example:
- ester of L-carnitine bromide with 2-hydroxyacetyl-1,3-dipalmitoyl glycerol (ST 770);
- ester of acetyl L-carnitine bromide with 2-hydroxyacetyl-1,3-dipalmitoyl glycerol (ST 771);
- ester of isobutyryl L-carnitine bromide with 2-hydroxyacetyl-1,3 dipalmitoyl glycerol (ST 773);
- ester of isovaleryl L-carnitine bromide with 2-hydroxyacetyl-1,3-dipalmitoyl glycerol (ST 774);
- ester of L-carnitine bromide with 1,3-dihexanoyl-2-hydroxyacetyl glycerol (ST 810);
- ester of acetyl L-carnitine bromide with 1,3-dihexanoyl-2-hydroxyacetyl glycerol (ST 809).
- propionyl L-carnitine bromide ester with 1,3-dihexanoyl-2-hydroxyacetyl glycerol (ST 808), One preferred embodiment of the invention described herein consists in the preparation of liposomes with anticancer drugs, and particularly liposomes that act as vehicles for camptothecins, for example those disclosed in WO 97/31003. In a more preferred embodiment, the invention described herein provides liposomes for delivering camptothecins with general formula (IV):

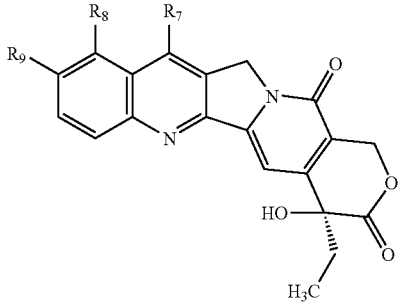

(IV)

where: $R_7$ is a —$C(R_{11})$=N—$O_{(n)}R_{10}$ group, in which $R_{10}$ is hydrogen or a $C_1$-$C_5$ alkyl or $C_1$-$C_5$ alkenyl group, straight or branched, or a $C_3$-$C_{10}$ cycloalkyl group, or a straight or branched ($C_3$-$C_{10}$) cycloalkyl-($C_1$-$C_5$) alkyl group, or a $C_6$-$C_{14}$ aryl, or a straight or branched ($C_6$-$C_{14}$) aryl-$C_1$-$C_5$) alkyl group, or a heterocyclic or straight or branched heterocycle-($C_1$-$C_5$) alkyl group, said heterocyclic group containing at least one heteroatom selected from atoms of nitrogen, optionally substituted by a ($C_1$-$C_5$) alkyl group, and/or oxygen and/or sulphur; said alkyl, alkenyl, cycloalkyl, aryl, arylalkyl, heterocyclic or heterocyclo-alkyl groups being optionally substituted with other groups selected from: halogen, hydroxy, $C_1$-$C_5$ alkyl, $C_1$-$C_5$ alkoxy, phenyl, cyano, nitro, —$NR_{12}R_{13}$, where $R_{12}$ and $R_{13}$, which may be the same or different, are hydrogen, straight or branched ($C_1$-$C_5$) alkyl, the —COOH group or one of its pharmaceutically acceptable esters; or the —$CONR_{14}R_{15}$ group, where $R_{14}$ and $R_{15}$, which may be the same or different, are hydrogen, straight or branched ($C_1$-$C_5$) alkyl; or $R_{10}$ is a $C_6$-$C_{10}$ aroyl residue, optionally substituted by one or more groups selected from: halogen, hydroxy, straight or branched $C_1$-$C_5$ alkyl, straight or branched $C_1$-$C_5$ alkoxy, phenyl, cyano, nitro, —$NR_{16}R_{17}$, where $R_{16}$ and $R_{17}$, which may be the same or different, are hydrogen, straight or branched $C_1$-$C_5$ alkyl;

$R_{10}$ is a polyaminoalkyl residue; or $R_{10}$ is a glycosyl residue;

n is the number 0 or 1;

$R_{11}$, is hydrogen, straight or branched $C_1$-$C_5$ alkyl, straight or branched $C_1$-$C_5$ alkenyl, $C_3$-$C_{10}$ cycloalkyl, straight or branched ($C_3$-$C_{10}$) cycloalkyl-($C_1$-$C_5$) alkyl, $C_6$-$C_{14}$ aryl, straight or branched ($C_6$-$C_{14}$) aryl-($C_1$-$C_5$) alkyl;

$R_8$ and $R_9$, which may be the same or different, are hydrogen, hydroxyl, straight or branched $C_1$-$C_5$ alkoxy;

their $N_1$-oxides, single isomers, particularly the syn and anti isomers of the —$C(R_{11})$=N—$O_{(n)}R_{10}$ group, their possible enantiomers, diastereoisomers and related mixtures, their pharmaceutically acceptable salts and their active metabolites.

Compounds of formula (IV) are described in European patent application no. 99830124.6, filed on 9 Mar. 1999.

As regards the compounds of formula (IV) in which n is 1 and $R_{10}$ is as defined above, with the exception of aroyl, these compounds can be prepared starting from camptothecin 7-aldehyde (formula IVa, $R_{11}$ hydrogen) o camptothecin 7-keto (formula IVa, $R_{11}$ other than hydrogen).

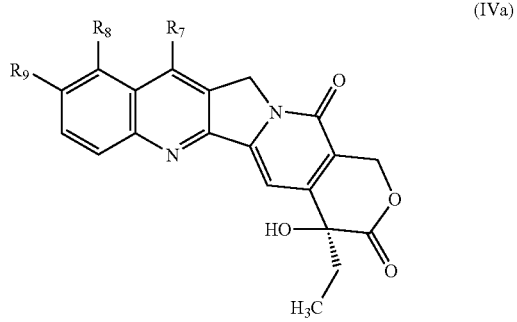

(IVa)

where $R_7$ is the —$C(R_{11})$=O group, and $R_{11}$ is as defined in formula (IV), $R_8$ and $R_9$ are as defined in formula (IV). The formula (IVa) compound is reacted with the formula (Va) compound $R_{10}O$—$NH_2$, where $R_{10}$ is as above, to yield compounds of formula (I), in which $R_7$ is the —$C(R_{11})$=N—O—$R_{10}$ group, $R_{10}$ is defined as in formula (IV), except for aroyl.

The reaction can be carried out with conventional methods known to experts in the field, the process consisting in the normal formation of oximes. Preferably, the molar ratio of camptothecin 7-aldehyde o 7-keto to hydroxylamine should be in the 1:3 to 3:1 range. The relevant hydroxylamine salts can also be used. The reaction is carried out in the presence of a base, for example, an inorganic base such as potassium carbonate, or an organic base, such as triethylamine or diazabicyclononane, using polar solvents, preferably methanol or ethanol, and carrying out the reaction at a temperature ranging from ambient temperature to the boiling point temperature of the solvent, optionally in the presence of dehydrating agents, e.g. sodium or magnesium sulphate, molecular sieves. If required, the reaction can also be carried out in the presence of a catalyst, e.g. a Lewis acid.

Alternatively, the above-mentioned compounds can be prepared from the oxime of camptothecin 7-aldehyde (obtained as described in Sawada et al Chem. Pharm. Bull. 39, 2574 (1991)), or 7-ketone or from the corresponding 7-acyl-camptothecin by reaction with an $R_{10}$—X halide, where X is preferably iodine, in a polar solvent, e.g. tetrahydrofuran or alcohols, and in the presence of a base, e.g. sodium hydride or potassium carbonate.

As regards the compounds of formula (IV) in which n is 1 and $R_{10}$ is aroyl, as defined in formula (IV), these compounds can be prepared starting from camptothecin 7-oxime, the preparation of which was described in the previous paragraph, with $R_{10}$—COCl acyl chlorides, in polar solvents, and in the presence of a base, preferably pyridine, or directly in pyridine, as described by Cho et al. J. Org. Chem. 62, 2230 (1997).

As regards the compounds of formula (IV) in which n is 0 and $R_{10}$ is as defined above, with the exception of aroyl, the compounds can be prepared starting from camptothecin 7-aldehyde (formula IVa, $R_{11}$ hydrogen) or camptothecin 7-keto (formula IVa, $R_{11}$ other than hydrogen).

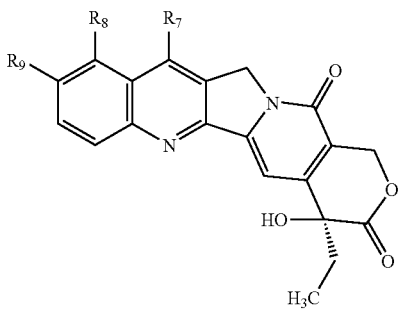

where $R_7$ is the —$C(R_{11})$=O group, and $R_{11}$ is as defined in formula (IV), $R_8$ and $R_9$ are as defined in formula (IV). The formula (IVa) compound is reacted with the formula (Vb) compound $R_{10}$—$NH_2$, where $R_{10}$ is as defined above, to yield compounds of formula (IV), in which $R_7$ is the —$C(R_{11})$=N—$R_{10}$ group, $R_{10}$ is defined as in formula (IV), except for aroyl. The reaction can be carried out with conventional methods known to experts in pharmaceutical technology, the process consisting in the normal formation of imines. Preferably, the molar ratio of camptothecin 7-aldehyde or 7-keto to imine should be in the 1:3 to 3:1 range. The relevant amine salts can also be used. The reaction is carried out in the presence of a base, for example, an inorganic base, such as potassium carbonate, or an organic base, such as triethylamine or diazabicyclononane, using polar solvents, preferably methanol or ethanol, and carrying out the reaction at a temperature ranging from ambient temperature to the boiling point temperature of the solvent, optionally in the presence of dehydrating agents, e.g. sodium or magnesium sulphate, molecular sieves. If required, the reaction can also be conducted in the presence of a catalyst, e.g. a Lewis acid as described, for example, by Moretti and Torre, *Synthesis*, 1970, 141; or by Kobayashi et al, Synlett, 1977, 115).

Camptothecin 7-aldehyde and camptothecin 7-oxime are described in European patent application EP 0056692 and in the above cited article by Sawada et al, Chem. Pharm. Bull. 39, 2574 (1991).

The $N_1$-oxides of the compounds of formula (IV) are prepared according to known heteroaromatic nitrogen oxidation methods, preferably by oxidation with acetic or trifluoroacetic acid and hydrogen peroxide, or by reaction with organic peroxyacids (A. Albini and S. Pietra, Heterocyclic N-oxides, CRC, 1991).

As regards the varying significance of $R_{10}$, present in the different formula V reagents, these reagents are commercially available, or can be prepared according to methods familiar from the literature, which the expert in the sector can resort to, as a supplement to his or her own knowledge of the subject.

Pharmaceutically acceptable salts are obtained with conventional methods described in the literature, and which require no further description.

EXAMPLE 8

7-benzyloxyiminomethylcamptothecin (CPT 172)

500 mg (1.33 mmol) of 7-formylcamptothecin are dissolved in 100 ml of ethanol. 15 ml of pyridine and 638 mg (4 mmol) of O-benzylhydroxylamine hydrochloride are added. The solution is refluxed for 5 hours. The solvent is vacuum evaporated and the residue thus obtained is purified by flash chromatography on silica gel using a 4:6 mixture of hexane/ethyl acetate as the eluant.

Yield: 65% m.p.: 200-205° C. dec.

The product obtained consists of an approximately 8:2 mixture of the two syn and anti isomers (isomer A: Rf 0.32; isomer B, Rf 0.19, on Merck 60 F254 silica gel; eluant: hexane:ethyl acetate 3:7).

HPLC: the analyses were carried out on an apparatus equipped with a quaternary pump (HP 1050) with a Rheodyne injector. (20 µl loop) and a diode-array detector (HP 1050) run by the HPLC-ChemStation program. Spectra acquisition was done from 200 to 600 nm and the chromatograms were recorded at 360 and 400 nm.

A C18 reverse-phase column (Rainin C18; 25×0.4 cm, Varian) was used with an RP18 precolumn. The analysis was carried out with a linear elution gradient, starting from acetonitrile:water 30:70 to acetonitrile 100% in 20 min, with a flow rate of 1 ml/min. The retention times were: 12.51 min for isomer B and 14.48 min for isomer A.

$^1$H-NMR (300 MHz; DMSO-$d_6$): δ: 0.88 (t, $H_3$-18A+$H_3$-18B), 1.878 m, ($H_2$-19A+$H_2$-19B), 5.18 (s, $H_2$-5B), 5.21 (8s, $H_2$-Ph B), 5.30 ($H_2$-Ph A), 5.40 (s, $H_2$-5A), 5.45 (s, $H_2$-17A+$H_2$-17B), 6.53 (s, —OH A+-OH B), 7.3-7.6 (m, Ar A+Ar B+H-14A+H-14B), 7.75 (m, H-11A+H-11B), 7.85-7-95 (m, H-10A+H-10B), 7.98 (dd, H-12B), 8.18-8.27 (m, H-12A+$H_9$-B), 8.45 (s, CH=N B), 8.59 (dd, H-9A), 9.38 (s, CH=N A).

Mass m/z 481 ($M^+$ 100) 374 (30) 330 (70) 300 (30) 273 (20) 243 (20) 91 (34).

EXAMPLE 9

7-butoxyiminomethylcamptothecin (CPT 184)

400 mg (1.06 mmol) of 7-formylcamptothecin are dissolved in 80 ml of ethanol. 12 ml of pyridine and 400 mg (3.18 mmol) of O-t-butylhydroxylamine hydrochloride are added. The solution is refluxed for 4 hours. The solvent is vacuum evaporated and the residue thus obtained is purified by flash chromatography on silica gel using a 4:6 mixture of hexane/ethyl acetate as the eluant.

322 mg (0.72 mmol) of yellow solid are obtained.

Yield: 68% m.p.: 250° C. dec.

The product obtained consists of an approximately 8:2 mixture of the two syn and anti isomers (isomer A: Rf 0.31; isomer B, Rf 0.24, on Merck 60 F254 silica gel; eluant: hexane:ethyl acetate 3:7).

HPLC: the analyses were carried out on an apparatus equipped with a quaternary pump (HP 1050) with a Rheodyne injector (20 µl loop) and a diode-array detector (HP 1050) run by the HPLC-ChemStation program. Spectra acquisition was done from 200 to 600 nm and the chromatograms were recorded at 360 and 400 nm.

A C18 reverse-phase column (Rainin C18; 25×0.4 cm, Varian) was used with an RP18 precolumn. The analysis was carried out with a linear elution gradient, starting from acetonitrile:water 30:70 to acetonitrile 100% in 20 min, with a flow rate of 1 ml/min. The retention times were: 12.92 min for isomer B and 14.61 min for isomer A.

$^1$H-NMR (300 MHz; DMSO-$d_6$): δ: 0.88 (t, $H_3$-18A+$H_3$-18B), 1.30 (s, t-but.B), 1.47 (s, t-but.A), 1.87 (m, $H_2$-19A+$H_2$-19B), 5.18 (s, $H_2$-5B), 5.37 ($H_2$-5 A), 5.42 (s, $H_2$-17A+$H_2$-17B), 6.54 (s, —OH A+-OH B), 7.35 (s H-14A), 7.36 (s, H-14B) 7.69-7.83 (m, H-11A+H-11B), 7.85-7.98 (m, H-10A+H-10B), 8.07 (dd, H-9B), 8.16-8.27 (m, H-9A+H-12B) 8.40 (s, CH B), 8.62 (dd, H-12A), 9.31 (s, CH A).

Mass m/z 448 ($M^+$ 28) 391 (40) 374 (100) 362 (40) 330 (34) 57 (17).

Preparation of Liposomes

The compounds according to the invention can be used to prepare multilamellar liposomes (MLV) and unilamellar liposomes (SUV), both in the form of dry powders and as suspensions in aqueous solutions.

The compounds according to the invention, prepared as described in examples 1-7, are used to prepare the liposomes according to the following procedure. A suitable amount of the compound is dissolved in chloroform; the solution is vacuum concentrated to dryness in a rotary evaporator until a lipid film is obtained. The lipid film is dried under high vacuum until the last remaining traces of solvent have been eliminated and then dissolved in tert-butylic alcohol or with water. The solution thus obtained is lyophilised, obtaining a soft, dry powder.

The powders are hydrated with a suitable amount of aqueous solution, obtaining the liposome of the compound used, which is then complexed with the polynucleotide or with the drug desired.

Another method of preparation of liposomes consists in adsorbing a lipid film, consisting of a compound according to the invention in a solvent, on a suitable inert support such as sorbitol, mannitol or other pharmacologically acceptable carbohydrates. The mixture is vacuum dried, obtaining a solid which can be easily and very rapidly hydrated prior to use.

Preparations in the form of dry powders present the advantage of being stable for long periods, and are easy to use.

Moreover, the compounds according to the invention can be used to prepare liposomes complexed with DNA or with the drug desired, in the form of dry powders, according to the following procedure. The compound according to the invention is dissolved in tert-butylic alcohol or with water; the solution thus obtained is mixed with DNA or the drug desired and the mixture is lyophilised, obtaining the complex which we can define as proliposome-DNA or proliposome-drug, in the form of a soft, dry powder.

The powders thus obtained (proliposomes) can be used for the preparation of pharmaceutical compositions which can be administered via aerosol, or which, alternatively, when reconstituted with water, or with a suitable buffer solution, can be administered parenterally or orally.

Liposomes complexed with DNA or with drugs, in solid form, can also be obtained with the method of adsorption of the lipid film on an inert support such as sorbitol, mannitol or other carbohydrates by means of the method described above.

Testing of Liposome Formation

Liposome formation was tested by means of a calorimetric method, using a water-soluble dye, according to the following procedure. An aqueous solution of the water-soluble dye Arsenazo III was obtained (m.w.=776.37; 2.3 mg/mL).

This solution was used instead of water to hydrate the lipid films coming from the above-mentioned preparation.

An aliquot of the suspension containing the liposome encapsulating the dye was diluted 100-fold with water.

Two mL of the liposome suspension were used to obtain the first optical density reading at 660 nm; the reading was obtained in relation to an equal sample defined as a blank. 200 µl of a $CaCl_2$ solution (15 mg/mL; 100 mM) were added to the first sample, and the optical density was measured at 660 nm against the blank, to which 200 µl of water were added. The absorbance value obtained was indicated as reading 2. We proceeded by adding to the sample 100 µl of a solution of Triton X-100 (5% v/v; 0.26% final concentration) and to the blank 200 µl of water; the optical density reading at 660 nm furnished the optical density value defined as reading 3. To calculate the percentage of encapsulated dye, the following formula was used:

$$\% \text{ dye encapsulated} = \frac{\text{Reading 3} - \text{Reading 2} \times 100}{\text{Reading 3}}$$

The percentage of encapsulated dye provides a measure of liposome formation and on average is approximately 40%: the liposome size check was performed using Laser Light Scattering with a positive outcome.

Examples of Preparation of Liposomes

Preparation of Liposomes of Palmitoyl L-carnitine Chloride Undecyl Ester (ST 983) in the Form of:

a) Lyophilised Powders 65 mg, 0.11 mmol of palmitoyl L-carnitine chloride undecyl ester were dissolved in 20 mL of chloroform, in a 100 mL flask.

The solution was evaporated until a lipid film was obtained which was vacuum dried for 3 hours The product thus obtained was dissolved in tert-butylic alcohol and this solution was rapidly cooled to −70° C. with liquid nitrogen and lyophilised for 24 hours.

A spongy soft white solid was obtained.

b) Adsorbed Powders 143 mg, 0.231 mmol of palmitoyl L-carnitine chloride undecyl ester were dissolved in 10 mL of chloroform. The solution thus obtained was poured in small portions into a 100 mL flask containing 750 mg of sorbitol. At the end of the addition of the various portions of chloroform solution, the chloroform was rapidly evaporated.

The solid thus obtained was vacuum dried for 3 hours.

893 mg of a solid white product were obtained.

Prior to use, the product is hydrated rapidly with a suitable volume of water to obtain an isotonic solution.

c) MLV Suspensions 65 mg, 0.11 mmol of palmitoyl L-carnitine chloride undecyl ester were dissolved in 20 mL of chloroform, in a 100 mL flask.

The solution thus obtained was evaporated until a lipid film was obtained which was then vacuum dried for 3 hours.

The lipid film was hydrated with 10 mL of water, at 30° C., for 3 hours, obtaining an MLV suspension.

The MLV suspension, suitably diluted, was complexed with a polynucleotide or with a drug and used for biological assays.

e) SUV Suspensions 65 mg, 0.11 mmol of palmitoyl L-carnitine chloride undecyl ester were dissolved in 20 mL of chloroform, in a 100 mL flask.

The solution thus obtained was evaporated until a lipid film was obtained which was then vacuum dried for 3 hours.

The lipid film was hydrated with 10 mL of water, at 30° C., for 3 hours, obtaining an MLV suspension.

The MLV suspension was extruded 10 times through a polycarbonate filter with a pore size of 200 nm. The unilamellar liposome suspension thus obtained was complexed with a polynucleotide or a drug and used for biological assays.

f) Testing of Physical Stability of Liposomes

The physical stability of the liposome suspension was tested by means of turbidimetry for a period of 30 days.

An absorbance measurement at 600 nm for a certain time interval was performed for each suspension to be tested. The mean absorbance value measured at time 0 remained constant for all the formulations tested.

The molecules considered presented compliant values over the time periods considered.

MLV and SUV liposome suspensions can be prepared by combining the compounds according to the invention with helper lipids such as cholesterol, 1-palmitoyl-2-oleoyl phosphatidyl choline (POPC) or dioleyl phosphatidyl choline (DOPE).

The compounds are combined with helper lipids for the purposes of obtaining liposomes with stabler membranes. Here below, in the section describing the preparation of liposomes, an example of a preparation is given, in which a compound according to the invention is combined with a helper lipid such as cholesterol or POPC.

Examples of Preparation of Liposomes for Drug Delivery

EXAMPLE 10

Preparation of taxol-ST 983 MLV liposomes (1:40)

20 mg, 0.0234 mmol of taxol and 556 mg, 0.9417 mmol of ST 983 were dissolved in 20 mL of chloroform.

The solution was concentrated until a lipid film was obtained on the surface of the glass flask.

After eliminating the last traces of chloroform with the aid of a vacuum pump, 20 mL of tert-butylic alcohol were added to the lipid film and the solution thus obtained was subdivided into 19 fractions which were immediately frozen at −70° C. with liquid nitrogen and lyophilised for 24 hours. Each fraction of solid contained taxol (1.05 mg) and ST 983 (29.2 mg).

To obtain the final liposome suspension, the lyophilised product was hydrated at the time of use with water (450 µL) or other saline solutions, stirred for 10 min and left to rest for 30 min to allow completion of the swelling (hydration) process.

MLV liposomes were obtained.

Testing of Physical Stability of the Preparation

The physical stability of the preparation was tested by means of turbidimetry with the recording of a TDC (Time Drive Curve) at 800 nm, at 20° C., for 20 hours.

A constant turbidity trend, indicative of stability of the preparation, was recorded, with no precipitation phenomena.

Testing of Chemical Stability of Taxol in the Preparation

The chemical stability of taxol was tested by HPLC.

The chromatographic conditions were as follows:

Column: µBondapack C-18

Eluent: acetonitrile:water 70:30

Detector UV-VIS: 227 nm

Flow rate: 1 mL/min

Retention time: 4.5 min

The taxol concentration, determined against a standard, was 2.13 mg/mL.

The percentage of encapsulated taxol was 98%.

EXAMPLE 11

Preparation of taxol-ST 983 SUV Liposomes 20 mg, 0.0234 mmol of taxol and 556 mg, 0.9417 mmol of ST 983 were dissolved 20 mL of chloroform.

The solution was concentrated until a lipid film was obtained on the surface of the glass flask.

After eliminating the last traces of chloroform with a high-vacuum pump, 20 mL of tert-butylic alcohol were added to the lipid film and the solution thus obtained was subdivided into 19 fractions which were immediately frozen at a −70° C. with liquid nitrogen and lyophilised for 24 hours. Each fraction of solid contained taxol (1.05 mg) and ST 983 (29.2 mg).

To obtain the final SUV liposome suspension the lyophilised product, hydrated with a PBS solution (1 mL), was sonicated for 20 min at 0° C.

Filtration was then performed on a 400 nm filter to eliminate traces of titanium released by the sonicator probe.

Testing of Physical Stability of the Preparation

The physical stability of the preparation was tested by means of turbidimetry with recording of a TDC (Time Drive Curve) at 800 nm, at 20° C., for 20 hours.

A constant turbidity trend, indicative of stability of the preparation, was recorded, with no precipitation phenomena.

Testing of Chemical Stability of Taxol in the Preparation

The chemical stability of taxol was tested by HPLC.

The chromatographic conditions were as follows:

Column: µBondapack C-18

Eluent: acetonitrile:water 70:30

Detector UV-VIS: 227 nm

Flow rate: 1 mL/min

Retention time: 4.5 min

HPLC analysis of the SUV liposome suspension yielded the same results as the corresponding MLV liposome suspension, and in this case, too, the percentage of encapsulated taxol was 98%.

HPLC analysis repeated after 24 hours revealed no new peaks other than the taxol peak, indicating stability of the active ingredient.

EXAMPLE 12

Preparation of Taxol-ST 983-Cholesterol Liposomes (1:15)

These types of liposomes were prepared in order to obtain complexes with stabler membranes.

6 mg, 0.0101 mmol of taxol, 62.2 mg, 0.105 mmol of ST 983 and 40 mg of cholesterol were dissolved in 10 mL of chloroform.

The solution thus obtained was concentrated until a lipid film was obtained on the surface of the glass flask.

After eliminating the last traces of chloroform with a high-vacuum pump, 6.3 mL of tert-butylic alcohol were added to the lipid film and the solution thus obtained was subdivided into 5 fractions which were immediately frozen at a −70° C.

with liquid nitrogen and lyophilised for 24 hours. Each fraction of solid contained taxol (1.2 mg), ST 983 (12.44 mg) and cholesterol (8 mg).

To obtain the final liposome suspension, the lyophilised product was hydrated at the time of use with water (1000 μL) or other saline solutions, stirred for 10 min and left to rest for 30 min to allow completion of the swelling (hydration) process.

MLV liposomes were obtained.

Testing of Physical Stability of the Preparation

The physical stability of the preparation was tested by means of turbidimetry with recording of a TDC (Time Drive Curve) at 800 nm, at 20° C., for 6 hours.

A constant turbidity trend, indicative of stability of the preparation, was recorded, with no precipitation phenomena.

EXAMPLE 13

Preparation of Taxol-ST 772 SUV Liposomes (1:70)

20 mg, 0.0234 mmol of taxol and 1485 mg, 1.638 mmol of ST 772 were dissolved in 20 mL of chloroform.

The solution was concentrated until a lipid film was obtained on the surface of the glass flask.

After eliminating the last traces of chloroform with a high-vacuum pump, 20 mL of tert-butylic alcohol were added to the lipid film. To obtain a clear solution, it had to be heated to 60° C. The solution was immediately frozen at a −70° C. with liquid nitrogen and lyophilised for 24 hours.

To obtain the final SUV liposome suspension the lyophilised product, hydrated with a PBS solution (20 mL), was sonicated for 20 min at 0° C.

Filtration was then performed on a 400 nm filter to eliminate traces of titanium released by the sonicator probe.

Testing of Physical Stability of the Preparation

The physical stability of the preparation was tested by means of turbidimetry with recording of a TDC (Time Drive Curve) at 800 nm, at 20° C., for 6 hours.

A constant turbidity trend, indicative of stability of the preparation, was recorded, with no precipitation phenomena.

EXAMPLE 14

Preparation CPT 83-ST 983 MLV Liposomes (1:40)

6.3 mg, 0.0168 mmol of CPT 83 (7-carbonitrile camptothecin, described in WO 97/31003) and 400 mg, 0.667 mmol of ST 983 were dissolved in 20 mL of chloroform.

The solution was concentrated until a lipid film was obtained on the surface of the glass flask.

After eliminating the last traces of chloroform with the aid of a vacuum pump, 26 mL of tert-butylic alcohol were added to the lipid film and the solution thus obtained was subdivided into 12 fractions which were immediately frozen at −70° C. with liquid nitrogen and lyophilised for 24 hours. Each fraction of solid contained CPT 83 (0.525 mg) and ST 983 (33.33 mg).

To obtain the final liposome suspension, the lyophilised product was hydrated at the time of use with water (1000 μL) or other saline solutions and stirred for 10 min.

MLV liposomes were obtained.

Testing of Physical Stability of the Preparation

The physical stability of the preparation was tested by means of turbidimetry with the recording of a TDC (Time Drive Curve) at 800 nm, at 20° C., for 20 hours.

A constant turbidity trend, indicative of stability of the preparation, was recorded, with no precipitation phenomena.

Testing of Chemical Stability of CPT 83 in the Preparation.

The chemical stability of CPT 83 was tested by HPLC.

The chromatographic conditions were as follows:

Column: Supelcosil LC-ABZ

Eluent: phosphate buffer 20 mM:methanol 40:60, pH=7.3

Detector UV-VIS: 360 nm

Flow rate: 1 mL/min

Retention time: 4.033 min

The CPT 83 concentration, determined against a standard, was 0.502 mg/mL.

The percentage of encapsulated CPT 83 was 99%.

EXAMPLE 15

Preparation of CPT 83-ST 983 SUV Liposomes (1:40)

6.3 mg, 0.0168 mmol of CPT 83 and 400 mg, 0.667 mmol of ST 983 were dissolved in 20 mL of chloroform.

The solution was concentrated until a lipid film was obtained on the surface of the glass flask.

After eliminating the last traces of chloroform with a high-vacuum pump, 26 mL of tert-butylic alcohol were added to the lipid film and the solution thus obtained was subdivided into 12 fractions which were immediately frozen at a −70° C. with liquid nitrogen and lyophilised for 24 hours. Each fraction of solid contained CPT 83 (0.525 mg) and ST 983 (33.33 mg).

To obtain the final SUV liposome suspension the lyophilised product, hydrated with water (1000 μL), was sonicated for 40 min at 0° C.

Filtration was then performed on a 400 nm filter to eliminate traces of titanium released by the sonicator probe.

Testing of Chemical Stability of CPT 83 in the Preparation

The chemical stability of CPT 83 was tested by HPLC.

The chromatographic conditions were as follows:

Column: Supelcosil LC-ABZ

Eluent: phosphate buffer 20 mM:methanol 40:60, pH=7.3

Detector UV-VIS: 360 nm

Flow rate: 1 mL/min

Retention time: 4.033 min

The CPT 83 concentration, determined against a standard, was 0.3 mg/mL.

The percentage of encapsulated CPT 83 was 59%.

HPLC analysis repeated after 24 hours revealed no new peaks other than the CPT 83 peak, indicating stability of the compound.

Testing of Physical Stability of the Preparation

The physical stability of the preparation was tested by means of turbidimetry with recording of a TDC (Time Drive Curve) at 600 nm, at 20° C., for 20 hours.

A constant turbidity trend, indicative of stability of the preparation, was recorded, with no precipitation phenomena.

EXAMPLE 16

Preparation of CPT 184-ST 983 MLV Liposomes (1:40)

7.29 mg, 0.0168 mmol of CPT 184 and 400 mg, 0.677 mmol of ST 983 were dissolved in 20 mL of chloroform.

The solution was concentrated until a lipid film was obtained on the surface of the glass flask.

After eliminating the last traces of chloroform with the aid of a vacuum pump, 26 mL of tert-butylic alcohol were added to the lipid film and the solution thus obtained was subdivided into 12 fractions which were immediately frozen at −70° C. with liquid nitrogen and lyophilised for 24 hours. Each fraction of solid contained CPT 184 (0.607 mg) and ST 983 (33.33 mg).

To obtain the final liposome suspension, the lyophilised product was hydrated at the time of use with water (1000 μL) or other saline solutions and stirred for 10 min.

MLV liposomes were obtained.

Testing of Physical Stability of the Preparation

The physical stability of the preparation was tested by means of turbidimetry with the recording of a TDC (Time Drive Curve) at 600 nm, at 20° C., for 20 hours.

A constant turbidity trend, indicative of stability of the preparation, was recorded, with no precipitation phenomena.

Testing of Chemical Stability of CPT 184 in the Preparation.

The chemical stability of CPT 184 was tested by HPLC.

The chromatographic conditions were as follows:

Column: Supelcosil LC-ABZ

Eluent: phosphate buffer 20 mM:methanol 40:60, pH 7.3

Detector UV-VIS: 360 nm

Flow rate: 1 mL/min

Retention time: 25.5 min

The CPT 184 concentration, determined against a standard, was 0.600 mg/mL.

The percentage of encapsulated CPT 184 was 99%.

EXAMPLE 17

Preparation of CPT 184-ST 983 SUV Liposomes (1:40)

7.29 mg, 0.0168 mmol of CPT 184 and 400 mg, 0.667 mmol of ST 983 were dissolved in 20 mL of chloroform.

The solution was concentrated until a lipid film was obtained on the surface of the glass flask.

After eliminating the last traces of chloroform with a high-vacuum pump, 26 mL of tert-butylic alcohol were added to the lipid film and the solution thus obtained was subdivided into 12 fractions which were immediately frozen at a −70° C. with liquid nitrogen and lyophilised for 24 hours. Each fraction of solid contained CPT 184 (0.607 mg) and ST 983 (33.33 mg).

To obtain the final SUV liposome suspension the lyophilised product, hydrated with water (1000 μL), was sonicated for 40 min at 0° C.

Filtration was then performed on a 400 nm filter to eliminate traces of titanium released by the sonicator probe.

Testing of Chemical Stability of CPT 184 in the Preparation

The chemical stability of CPT 184 was tested by HPLC.

The chromatographic conditions were as follows:

Column: Supelcosil LC-ABZ

Eluent: phosphate buffer 20 mM:methanol 40:60, pH=7.3

Detector UV-VIS: 360 nm

Flow rate: 1 mL/min

Retention time: 25.5 min

The CPT 184 concentration, determined against a standard, was 0.36 mg/mL.

The percentage of encapsulated CPT 184 was 70%.

HPLC analysis repeated after 24 hours revealed no new peaks other than the CPT 184 peak, indicating stability of the active ingredient.

Testing of Physical Stability of the Preparation

The physical stability of the preparation was tested by means of turbidimetry with recording of a TDC (Time Drive Curve) at 600 nm, at 20° C., for 20 hours.

A constant turbidity trend, indicative of stability of the preparation, was recorded, with no precipitation phenomena.

In the following examples, liposomes were prepared by using helper lipids and/or cryoprotecting agents.

EXAMPLE 18

Preparation of CPT 184-ST 983 Liposomes

In a 2 l flask, 100 ml of methylchloroform were added to 20 mg of CPT 184 and 600 mg of ST 983 and the mixture was slightly warmed until complete dissolution. The solution obtained was concentrated in a rotavapor until a lipid film was obtained, which was further dried for two hours at a high-vacuum pump. The lipid film was hydrated with a lactose solution (6 g/300 ml water) at 45° C. and left under stirring in the rotavapor for about 2 hours. The suspension was then sonicated for 2 hours, each cycle lasting half an hour. Subsequently, the product was filtered through a 200 nm filter and lyophilised.

Testing of Chemical Stability of CPT 184 in the Preparation

The chemical stability of CPT 184 was ascertained by HPLC. The product was stable during 24 hours of the test.

Testing of Physical Stability of the Preparation

The physical stability of the preparation was tested by means of turbidimetry. The product was stable throughout the 24 hours of the test. Particle size also was stable (mean value of 100 nm).

EXAMPLE 19

Preparation of CPT 184-ST 983 Liposomes

For 1 ml of liposomal formulation (POPC—1-palmitoyl-2-oleoyl phosphatidyl choline 5 mM; ST 983 1.25 mM; CPT 184 0.25 and trehalose 150 mM), the following procedure was used:

0.11 mg, 0.25 μmoles of CPT 184 were dissolved into 250 μL ethyl acetate, 3.79 mg, 4.89 μmoles of POPC were dissolved into 100 μL ethanol and 0.74 mg, 1.25 μmoles of ST 983 were dissolved into 100 μL ethanol. The three solutions were mixed together and vortexed. The solvents were evaporated off with a rotavapor at room temperature, 80 mbar. The lipid film was dried for two hours in the dark. The lipid film was suspended in a 1 ml of a 150 mM D(+)-trehalose dihydrate (Fluka, HPLC 99%) solution, sterilised through a 0.22 nm filter and vortexed for two minutes. The suspension was extruded 21 times through 200 nm polycarbonate filters. The extruded liposome suspension was frozen in liquid nitrogen and lyophilised for 2 nights. A white solid was obtained.

EXAMPLE 20

Preparation of CPT 184-ST 983 Liposomes

The same procedure of Example 19 was used, except trehalose 500 mM was used.

Anticancer Activity of ST 983 Liposome-Anticancer Agent Complex

As will be seen here below, the ST 983 liposome showed predominant accumulation at the pulmonary level. This characteristic of site-specificity has favoured its use in a murine model of pulmonary carcinogenesis.

The anticancer agent used in this experiment was taxol.

To induce the tumour in vivo, unanaesthetised Balb/c mice received injections of $3 \times 10^5$ cells of murine pulmonary carcinoma M109 in 0.1 ml RPMI-1640 (Sigma) in the quadriceps femoris of the right rear paw.

Ten days after implantation of the tumour the liposome-taxol complex was diluted with phosphate-buffered saline solution (PBS, SIGMA, P-4417) and injected intravenously at a concentration of 2.5 mg/mL of ST 983 and 75 µg/mL of taxol.

Taxol (paclitaxel INDENA) used as a control was dissolved in the cremophor vehicle EL (BASF) at a concentration of 20 mg/mL and stored at +4° C. for the next 24 hours, protected against the light. At the time of use, it was diluted with phosphate-buffered saline solution (PBS, SIGMA) and injected intravenously in the same volume and concentration conditions as described for taxol transported by the ST 983 liposome.

The cremophor was prepared by diluting 1:1 with ethyl alcohol.

Administrations were given for seven consecutive days starting from day 10 after inoculation of the tumour. The animals were kept under observation up to day 17 post-inoculation and sacrificed by cervical dislocation, and their lungs were removed for determination of the number of metastases. Staining of the lungs to detect metastases was done by incubating the lungs for 10 days in 5 ml of Bouin's solution, consisting of 71% saturated picric acid solution, 4.8% glacial acetic acid (Merck), and 24% 10% formaldehyde (Fluka). At the end of the incubation period in Bouin's solution, the numbers of metastases were counted.

As compared to the untreated control mice, the cremophor-transported taxol showed no reducing effect on the number of pulmonary metastases, though the latter were smaller than those of the untreated controls, whereas taxol complexed with the ST 983 liposome showed a significant reduction in both the number and size of pulmonary metastases.

Statistical analysis of the data for the number of lung metastases was done using the Mann-Whitney non-parametric tests for unpaired data.

The results obtained are presented in Table 1 here below.

TABLE 1

Lung metastases at $17^{th}$ day after M109 tumor inoculation in BALB/c mice after treatment with taxol and taxol/liposome ST983.

| Group | metastases Mean ± s.d | metastases size |
|---|---|---|
| Controls | 21 ± 12 | M |
| Taxol | 22 ± 9 | S |
| Taxol-ST983 | 10 ± 2 | S |

M = mean (1–2 mm diameter)
S = small (<1 mm diameter)

In-Vitro Cytotoxicity Tests

The toxicity assays were done on HeLa and M109 cells in 96-well plates. On the day after plating, the cells were treated with the molecules being tested for the next 48 hours. The cells were then washed with PBS and left in normal growth conditions for 48 hours. After removal of the growth medium, the cells were incubated on ice with 16% TCA, washed 3 times in $H_2O$, treated for 30 minutes with sulforhodamine B (SRB) in 1% acetic acid, washed 3 times in 1% acetic acid alone, incubated for 20 minutes in TRIS 10 mM pH 10.5 and, lastly, readings were taken at 540 mm.

Cytotoxicity Tests with CPT 83

In-vitro Cytotoxicity tests with CPT 83 were conducted in order to evaluate the cytotoxicity of the anticancer agent complexed with the liposome, as a preliminary indication of efficient activity.

To evaluate the ability of the liposome to transport CPT 83 in vitro in M109 cells the sulforhodamine B test described above was used.

In addition, the cytotoxicity of CPT 83 dissolved in dimethyl-sulphoxide (DMSO) was also evaluated as compared to that of the same molecule complexed with the ST 983 liposome.

The liposome-CPT 83 complex was used in the cytotoxicity assays at the concentrations indicated in Tables 2.1, 2.2 and 3.3 here below in both the SUV and MLV configurations. The liposome:CPT 83 molar ratio used was 40:1.

The mean cytotoxicity values of the ST 983-CPT 83 complexes in both the SUV and MLV configurations given in Tables 2.1, 2.2 and 2.3 here below, indicate that the ST 983 liposome is capable of transporting CPT 83 in much the same way as DMSO, presenting cytotoxicity levels of the same order of magnitude.

TABLE 2.1

Cytotoxicity (SRB) of ST 983 SUV-CPT 83 Concentrations in µM

|  | ctr | 1.3 | 0.13 | 0.013 | 00013 |
|---|---|---|---|---|---|
|  | 0.911 | 0.294 | 0.705 | 0.908 | 0.911 |
|  | 0.745 | 0.198 | 0.525 | 0.821 | 0.83 |
|  | 0.884 | 0.204 | 0.801 | 0.906 | 0.91 |
|  | 0.833 | 0.25 | 0.748 | 0.856 | 0.853 |
|  | 0.854 | 0.254 | 0.778 | 0.867 | 0.873 |
|  | 0.793 | 0.231 | 0.739 | 0.802 | 0.803 |
|  | 0.792 | 0.193 | 0.602 | 0.827 | 0.829 |
|  | 0.901 | 0.248 | 0.69 | 0.904 | 0.89 |
| Mean | 0.839125 | 0.352444 | 0.635333 | 0.767111 | 0.7667 |
| s.d. | 0.060645 | 0.034513 | 0.092925 | 0.042054 | 0.040149 |

The values given in the table refer to the optical density readings at 540 nm.

TABLE 2.2

Cytotoxicity (SRB) of ST 983 MLV-CPT 83

| | | concentrations in μM | | |
|---|---|---|---|---|
| Ctr | 1.3 | 0.13 | 0.013 | 0.0013 |
| 0.895 | 0.038 | 0.04 | 0.095 | 0.088 |
| 0.82 | 0.038 | 0.046 | 0.109 | 0.124 |
| 0.896 | 0.041 | 0.049 | 0.128 | 0.127 |
| 0.847 | 0.041 | 0.042 | 0.105 | 0.115 |
| 0.863 | 0.041 | 0.053 | 0.111 | 0.107 |
| 0.794 | 0.043 | 0.041 | 0.073 | 0.095 |
| 0.829 | 0.039 | 0.044 | 0.08 | 0.085 |
| 0.893 | 0.041 | 0.044 | 0.064 | 0.065 |
| mean 0.854625 | 0.04025 | 0.044875 | 0.095625 | 0.10075 |
| s.d. 0.038682 | 0.001753 | 0.004357 | 0.021738 | 0.021359 |

The values given in the table refer to the optical density readings at 540 nm.

TABLE 2.3

Cytotoxicity (SRB) of DMSO-CPT 83:

| | | Concentrations in μM | | | |
|---|---|---|---|---|---|
| ctr | 13 | 1.3 | 0.13 | 0.013 | 0.0013 |
| 0.898 | 0.281 | 0.33 | 0.406 | 0.8 | 0.809 |
| 0.774 | 0.267 | 0.302 | 0.407 | 0.804 | 0.816 |
| 0.857 | 0.3 | 0.285 | 0.57 | 0.863 | 0.886 |
| 0.787 | 0.286 | 0.287 | 0.383 | 0.836 | 0.841 |
| 0.808 | 0.285 | 0.318 | 0.474 | 0.851 | 0.863 |
| 0.745 | 0.288 | 0.317 | 0.467 | 0.79 | 0.795 |
| 0.775 | 0.312 | 0.328 | 0.429 | 0.806 | 0.831 |
| 0.864 | 0.318 | 0.305 | 0.421 | 0.81 | 0.878 |
| Mean 0.8135 | 0.292125 | 0.309 | 0.444625 | 0.82 | 0.839875 |
| s.d. 0.053519 | 0.016848 | 0.017205 | 0.059269 | 0.026506 | 0.033237 |

The values given in the table refer to the optical density readings at 540 nm.

Biological Activity of ST 983 Liposome-CPT 184 Complex

The biological activity of liposomes of example 18 (below named liposome A) and of example 20 (below named liposome B) was tested.

Toxicity in Healthy Mouse

Liposomes A and B were given orally, intravenously, in comparison with free CPT 184, at the dose of 1.2 mg/kg according to the q4dx4 scheme. The two liposomes did not have significant effects on the weight of body, lungs, spleen and kidneys. Liposome B, intravenously, and liposome A, orally given affected thymus weight similarly to free CPT 184. Intravenous liposome A had only a minimum effect. Haematological parameters did not show significant variations after 24 hours, with both liposomes. Liposome A, intravenously give according to qd5 scheme showed a toxicity comparable with free CPT 184.

Lung Tropism of Liposomes

Figure 3:
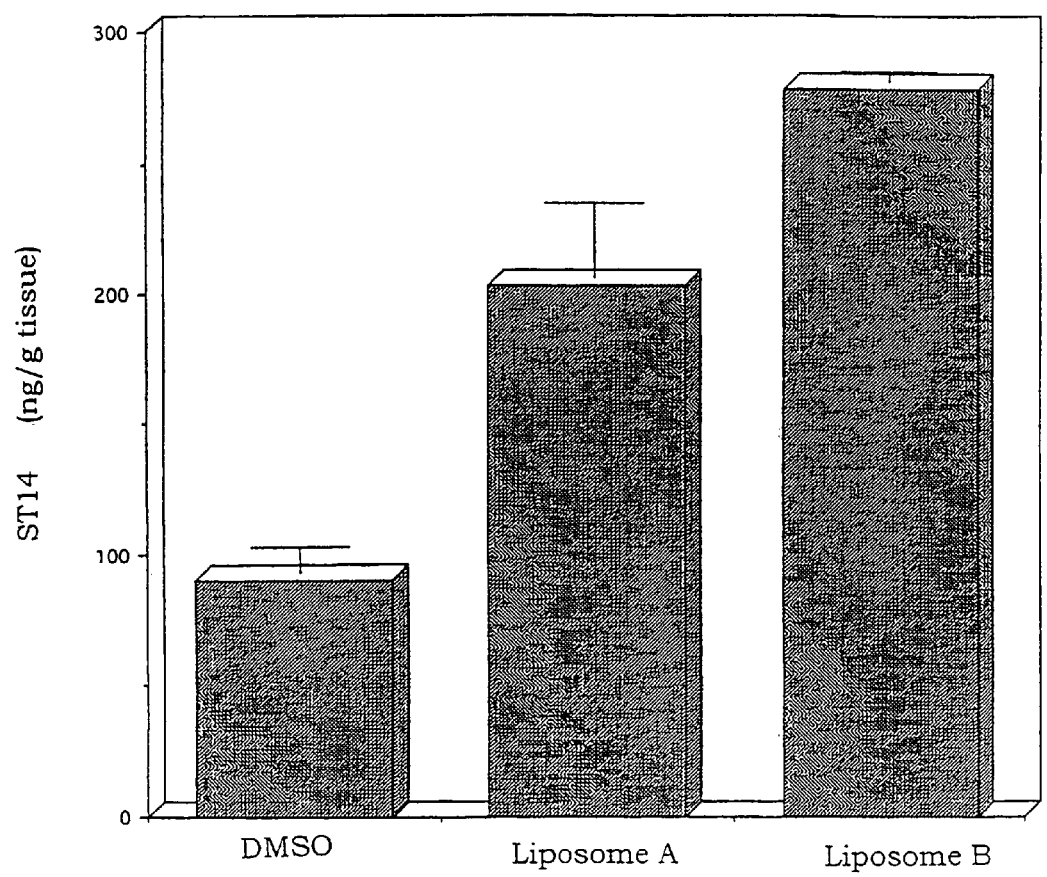
FIG. 3 shows tissue contents (lung) of ST1481-liposomes delivered in i.v. injected mice (q4dx4).

Liposomes A and B showed predominant accumulation at the pulmonary level. The liposomes were given i.v. 1.2 mg/kg. Free CPT 184 was given orally 1.2 mg/kg in DMSO. The animals, healthy mice, were sacrificed 24 hours after the last administration. Lungs were excised from the corps and frozen in liquid nitrogen. Once thawed, the organs were pooled and homogenised in a 0.1% acetic acid/acetonitrile 1:5. Homogenates were divided in three aliquots, two of them were added with CPT 184 for recovery calculation. The three samples were centrifuged at 16,000 g for 5 minutes. Surnatants were gathered and extracted with dichloromethane. The organic phase was dried with a speedvac and the residue was redissolved in acetonitrile in order to have the amount corresponding to one animal in 50 μL for loading in HPLC. HPLC was run on a Waters Symmetry C18 3.5 μm (4.6×7.5 mm). A Merck fluorimeter was the detector at 370 nm excitation and 510 nm emission. The eluant was water/acetonitrile 60:40, isocratic. Sample volume was 50 μL. CPT 184 recovery was about 70%. Both liposome A and B gave an accumulation level for CPT 184 higher than free CPT 184 in DMSO, as shown in FIG. 3.

Gene Delivery

Preparation of Liposome-DNA Complex

Liposome and plasmid DNA were suitably diluted separately in PBS. The DNA was then added to the liposome and the liposome-DNA complex was left for approximately 30 min at 4° C. to facilitate the formation of a stable liposome-DNA interaction.

In the in-vitro experiments, 1,2-dioleoyloxy-3-trimethyl-ammonium propane (DOTAP) was used as a reference cationic lipid; 2.5 μg of plasmid DNA were used per $2 \times 10^5$ HeLa cells, and the liposome concentration was 9 μM.

In the in-vivo experiments, both DOTAP and [2,3-(dioleoyl)propyl]trimethylammonium (DOTMA) were used as reference cationic lipids.

The molar ratios defined in the results refer to nmol concentrations of the respective cationic lipids per mg of DNA.

In the in-vivo transfection experiments, 25 μg of plasmid DNA per animal were used.

The plasmid pCMVluc used in these experiments contained the cDNA of the luciferase gene under the transcriptional control of the cytomegalovirus (CMV) promoter.

Quantitative Determination of Luciferase Activity

Protein luciferase activity in cells and tissues was determined using the Boehringer Mannheim kit (cat no. 1669 893).

The cells were washed 3 times in PBS and then removed from the plate with a scraper in lysis buffer (100 mM potassium phosphate pH 7.8. 1 mM dithiothreitol—DTT) and submitted to three consecutive cycles of freezing and thawing. After centrifuging in 1.5 mL Eppendorf tubes, the supernatant was used for the luminescence test not more than 5 hours after extraction of the proteins. Luminescence emission measurements were done using a luminometer at 562 nm. After a first freezing in liquid $N_2$ followed by is fine crushing to obtain a powder, the tissues were resuspended in lysis buffer and incubated for 10-15 min in ice.

The samples were then centrifuged in 2 ml Eppendorf tubes and the supernatant was tested for luciferase activity.

Dot-Blot Analysis

Cellular DNA was extracted according to the alkaline lysis procedure described by Sanbrook, Fritsch and Maniatis in Molecular Cloning, 1989.

5 μg of the DNA extracted from the cells were preabsorbed on nylon filters (Boehringer) using the Biorad dot-blot appliance. The filters were then prehybridised for 4 hours at 65° C. with a solution containing 0.5 M of sodium pyrophosphate (NaPi), 1 mM EDTA, 7% SDS. The probe labelled with $^{32}P$(alpha) was prepared using plasmid pCMVluc DNA as a template and the random primed Amersham Kit. The filter was hybridised in the same prehybridisation buffer for 12 hours at 42° C. using $1 \times 10^6$ CPM/ml. The filter was then submitted to 3 10-min washings at 65° C. in a buffer containing 40 mM. NaPi, 1% SDS. The autoradiographic analysis was carried out with the aid of a phosphor imager which uses phosphor screens activated by beta-radiation which are read and quantified by means of a photomultiplier system in conjunction with an image analysis program. The densitometry performed on the dot blot was done is using an IP-LabGel image analysis program.

Plasmid DNA Transfection Tests

A number of plasmid DNA transfection tests were carried out both in vitro and in vivo.

Both DOTAP and DOTMA were used as reference cationic lipids, the transfection capacity of which has been amply characterised and described by Abkenet et al., Proc. Natl. Acad. Sci. USA 1993, 90, 6518. In the in-vivo experiments, various different molar ratios of cationic lipids to plasmid DNA were analysed for the purposes of determining the activity of the cationic lipids and the respective most efficient concentrations for gene transfer. The transfection capability of the various liposomes was evaluated both in vitro and in vivo using the luciferase gene transporter contained in the pCMVluc plasmid, the activity of which, in terms of relative luminescence units (RLU) (described previously) made for easy quantification.

As an alternative, the transfection efficiency of a number of cationic liposomes was evaluated by means of densitometric analysis (phosphor imager) of samples of DNA extracted from transfected cells preabsorbed on nitrocellulose filters (dot-blot) and hybridised with $^{32}P$-labelled plasmid DNA markers, as described previously.

In-Vivo Transfection Tests

Dependence of In-Vivo Transfection Efficiency on ST 983 Liposome:DNA Molar Ratio In this experiment, the dependence of liver, lung and heart transfection efficiency on the ST 983 liposome:plasmid DNA molar ratio was evaluated. The following nmol ratios of liposome per μg DNA were tested: 12:1, 24:1, 36:1 and 48:1.

Groups of 6 Balb/c mice weighing approximately 20 g were treated intravenously with the above-mentioned amounts of liposome-DNA complex in 200 μl volumes of PBS and were sacrificed 24 hours after administration of the complex.

The luciferase activity extracted from the lung, heart and liver tissue revealed a predominantly pulmonary distribution of luciferase at all the molar ratios analysed. In fact, approximately 99% of the total luciferase extracted from the three tissues was located in the lungs. The liposome:DNA molar ratio of 12:1 proved to be the best. The results obtained are presented in Table 3 here below.

TABLE 3

In-vivo transfection efficiency of ST 983 as a function of ST 983:DNA molar ratio (μg DNA)

| Liposome | Mean RLU/mg protein ± s.d. | | | ST 983:DNA molar ratio |
| | liver | Lung | heart | |
| --- | --- | --- | --- | --- |
| ST 983 | 2589 +/− 140 | 8818442 +/− 449529 | 28875 +/− 2593 | 12:1 |
| | 1310 +/− 385 | 2257856 +/− 280480 | 7091 +/− 249 | 24:1 |
| | 1035 +/− 347 | 301107 +/− 21503 | 8351 +/− 477 | 36:1 |
| | 1571 +/− 156 | 112747 +/− 5655 | 5251 +/− 489 | 48:1 |
| Control | 396 +/− 55 | 458 +/− 45 | 755 +/− 55 | |
| DOTMA | 1352 +/− 226 | 3828742 +/− 161332 | 3363 +/− 123 | 12:1 |

Dependence of In-Vivo Transfection Efficiency on Differences Between SRT 983 Liposome Preparations Luciferase activity values, as relative luminescence units (RLU), extracted from the lungs of Balb/c mice treated intravenously with different ST 983 liposome preparations at a liposome:DNA molar ratio of 12:1, are reported in Table 4.

The data obtained, in addition to demonstrating that the ST 983 liposome is capable of transporting plasmid DNAI in vivo, with efficiency ratings higher than and/or comparable to those of DOTMA, also show a degree of variability among the different ST 983 preparations. This may be due to a number of physicochemical characteristics such as the size of the liposomal vesicles, or the relative proportions of the vesicles in relation to the unilamellar (SUV) or multilamellar structure of the different ST 983 preparations. In point of fact, the physicochemical parameters listed above have been amply described as determinants in achieving optimal in-vivo and in-vitro transfection efficiency by R. I. Mahato et al., Human Gene Therapy 9. 1998: 2083.

TABLE 4

In-vivo transfection efficiency of ST 983 (different preparations)

| Liposome | Mean RLU/mg protein ± s.d. Lung | ST 983:DNA Molar ratio |
| --- | --- | --- |
| ST 983/#72 | 3118235 +/− 184726 | 12:1 |
| ST 983/#73 | 7285835 +/− 827067 | 12:1 |
| ST 983/#4 | 1022117 +/− 60402 | 12:1 |
| Control | 1523 +/− 98 | |
| DOTMA | 3410125 +/− 189520 | 12:1 |

Dependence of In-Vivo Transfection Efficiency on ST 983-DNA Liposome Complex Preincubation Time Table 5 presents the relative luminescence units extracted from the liver, lung and heart of mice treated intravenously with ST 983 liposome preincubated with plasmid DNA for 30 minutes or for 3 hours prior to administration. The animals treated with ST 983 preincubated for 3 hours with DNA show an approximately 5-fold increase in luciferase activity in the lung and heart as compared to those treated with the same liposome preincubated for 30 minutes. This result suggests that the formation of a stable liposome-DNA complex is a time-dependent phenomenon and plays a critical role as a determinant of in-vivo transfection efficiency.

TABLE 5

Efficiency of in-vivo transfection of ST 983 as a function of liposome/DNA preincubation time

| Liposome | Time | Mean RLU/mg protein ± s.d. | | | T 983:DNA molar ratio |
| --- | --- | --- | --- | --- | --- |
| | | liver | Lung | heart | |
| ST 983 | 30 min. | 3526 +/− 260 | 874882 +/− 65917 | 8118 +/− 263 | 12:1 |
| ST 983 | 3 h | 2497 +/− 682 | 4225656 +/− 211731 | 37100 +/− 1853 | 12:1 |

Plasmid DNA Transfection in HeLa Cells with ST 772 Liposome

Figure 2:
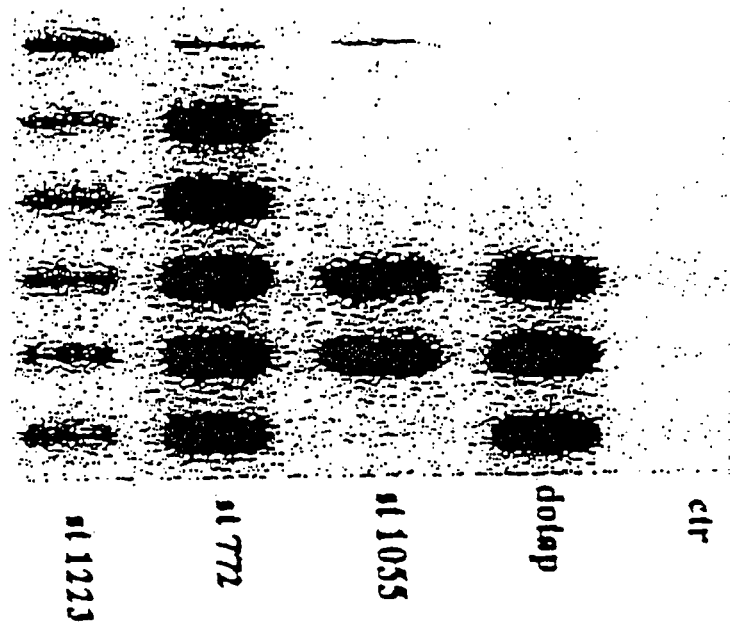
FIG. 2 shows the plasmid DNA transfection efficiency of the ST 772 liposome in HeLa cells (blot analysis)

FIGS. 1 and 2 show the plasmid DNA transfection efficiency of the ST 772 liposome in HeLa cells. For this purpose, densitometric analysis of the DNA extracted from the cells transfected with ST 272 and with DOTAP as the reference cationic lipid was carried out. The results of the blot analysis reveal amounts of plasmid DNA of the same order of magnitude as obtained with DOTAP.

The invention claimed is:
1. A method of intracellular delivery into tumor cells of taxol or a camptothecin derivative of formula

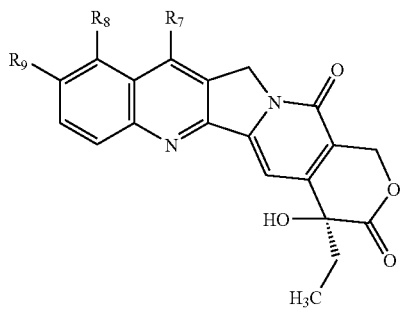

wherein: $R_7$ is a $-C(R_{11})=N-O_{(n)}R_{10}$ group, wherein $R_{10}$ is hydrogen or a $C_1-C_5$ alkyl or $C_2-C_5$ alkenyl group, linear or branched or $C_3-C_{10}$ cycloalkyl, group or a linear or branched $(C_3-C_{10})$ cycloalkyl-$(C_1-C_5)$ alkyl group, or $C_6-C_{14}$ aryl, or a linear or branched $(C_6-C_{14})$ aryl-$(C_1-C_5)$ alkyl group, or a heterocyclic or linear or branched heterocyclo-$(C_1-C_5)$ alkyl group, said heterocyclic group containing at least a heteroatom selected from the group consisting of nitrogen atom, optionally substituted with a $(C_1-C_5)$ alkyl group, and/or oxygen and/or sulfur; said alkyl, alkenyl, cycloalkyl, cycloalkylalkyl, aryl, aryl-alkyl, heterocyclic or heterocyclo-alkyl groups, being optionally substituted with other groups selected from the group consisting of: halogen, hydroxy, $C_1-C_5$ alkyl, $C_1-C_5$ alkoxy, phenyl, cyano, nitro, $-NR_{12}R_{13}$, wherein $R_{12}$ and $R_{13}$, which may be the same or different, are hydrogen, linear or branched ($C_1$-$C_5$) alkyl; a pharmaceutically acceptable ester of the $-COOH$ group; or the $-CONR_{14}R_{15}$ group, wherein $R_{14}$ and $R_{15}$, which may be the same or different, are hydrogen or linear or branched ($C_1$-$C_5$) alkyl; or $R_{10}$ is a ($C_6$-$C_{10}$) aroyl residue optionally substituted by one or more groups selected from the group consisting of: halogen, hydroxy, linear or branched ($C_1$-$C_5$) alkyl, $C_1$-$C_5$ alkoxy, phenyl, cyano, nitro, $-NR_{16}R_{17}$, wherein $R_{16}$ and $R_{17}$, which may be the same or different, is hydrogen, linear or branched ($C_1$-$C_8$) alkyl;

n is the number 0 or 1;

$R_{11}$ is hydrogen, linear or branched $C_1$-$C_5$ alkyl, linear or branched $C_2$-$C_5$ alkenyl, $C_3$-$C_{10}$ cycloalkyl, $(C_3$-$C_{10})$ cycloalkyl-linear or branched $(C_1$-$C_5)$ alkyl, $C_6$-$C_{14}$ aryl, $(C_6$-$C_{14})$ aryl-linear or branched alkyl $(C_1$-$C_5)$;

$R_8$ and $R_9$, which may be the same or different are hydrogen, hydroxy, linear or branched $C_1$-$C_5$ alkoxy;

their $N_1$-oxides, their single isomers, in particular the syn and anti isomers of the $-C(R_{11})=N-O_{(n)}R_{10}$ group, their enantiomers, diastereoisomers and admixtures, the pharmaceutically acceptable salts thereof;

using a liposome comprising a compound of formula (II)

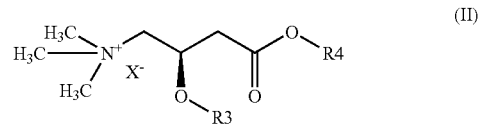

where:

$R_3$ is an acyl chain selected from the group consisting of palmitoyl and stearoyl;

$R_4$ is undecyl; the molar ratio between the compound of the formula (II) and the taxol or the camptothecin is 40:1; and $X^-$ is the anion of a pharmacologically acceptable acid.

2. The method according to claim 1, in which $X^-$ is selected from the group consisting of chloride; bromide; iodide; aspartate; citrate; tartrate; phosphate; fumarate; glycerophosphate; glucose phosphate; lactate; maleate; mucate; orotate; oxalate; sulphate; trichloroacetate; trifluoroacetate; methane sulphonate; and pamoate.

3. The method according to claim 1, in which the compound of formula (II) is selected from the group consisting of palmitoyl L-carnitine chloride undecyl ester; and stearoyl L-carnitine chloride undecyl ester.

4. The method according to claim 1, in which said derivative of camptothecin is selected from the group consisting of 7-benzyloxyiminomethylcamptothecin or 7-t-butoxyiminomethylcamptothecin.

5. The method according to claim 1, in which the liposome additionally contains helper lipids.

6. The method according to claim 5, in which said helper lipid is selected from the group consisting of cholesterol, 1-palmitoyl-2-oleoyl phosphatidyl choline or dioleyl phosphatidyl choline.

7. A composition comprising a liposome comprising a compound of formula (II)

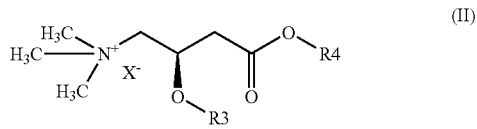

(II)

where:
R₃ is an acyl chain selected from the group consisting of palmitoyl and stearoyl;
R₄ is undecyl; and
X⁻ is the anion of a pharmacologically acceptable acid,
said liposome comprising taxol or a camptothecin derivative of formula

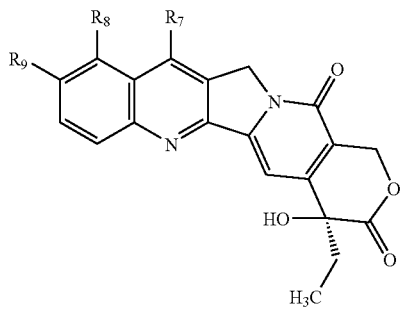

wherein: $R_7$ is a —C($R_{11}$)═N—O$_{(n)}R_{10}$ group, wherein $R_{10}$ is hydrogen or a $C_1$-$C_5$ alkyl or $C_2$-$C_5$ alkenyl group, linear or branched or $C_3$-$C_{10}$ cycloalkyl, group or a linear or branched ($C_3$-$C_{10}$) cycloalkyl-($C_1$-$C_5$) alkyl group, or $C_6$-$C_{14}$ aryl, or a linear or branched ($C_6$-$C_{14}$) aryl-($C_1$-$C_5$) alkyl group, or a heterocyclic or linear or branched heterocyclo-($C_1$-$C_5$) alkyl group, said heterocyclic group containing at least a heteroatom selected from the group consisting of nitrogen atom, optionally substituted with a ($C_1$-$C_5$) alkyl group, and/or oxygen and/or sulfur; said alkyl, alkenyl, cycloalkyl, cycloalkylalkyl, aryl, aryl-alkyl, heterocyclic or heterocycloalkyl groups, being optionally substituted with other groups selected from the group consisting of: halogen, hydroxy, $C_1$-$C_5$ alkyl, $C_1$-$C_5$ alkoxy, phenyl, cyano, nitro, —NR$_{12}$R$_{13}$, wherein $R_{12}$ and $R_{13}$, which may be the same or different, are hydrogen, linear or branched ($C_1$-$C_5$) alkyl; a pharmaceutically acceptable ester of the —COOH group; or the —CONR$_{14}$R$_{15}$ group, wherein $R_{14}$ and $R_{15}$, which may be the same or different, are hydrogen or linear or branched ($C_1$-$C_5$) alkyl; or $R_{10}$ is a ($C_6$-$C_{10}$) aroyl residue optionally substituted by one or more groups selected from the group consisting of: halogen, hydroxy, linear or branched ($C_1$-$C_5$) alkyl, $C_1$-$C_5$ alkoxy, phenyl, cyano, nitro, —NR$_{16}$R$_{17}$, wherein $R_{16}$ and $R_{17}$, which may be the same or different, are hydrogen, linear or branched ($C_1$-$C_8$) alkyl;

n is the number 0 or 1;

$R_{11}$ is hydrogen, linear or branched $C_1$-$C_5$ alkyl, linear or branched $C_2$-$C_5$ alkenyl, $C_3$-$C_{10}$ cycloalkyl, ($C_3$-$C_{10}$) cycloalkyl-linear or branched ($C_1$-$C_5$) alkyl, $C_6$-$C_{14}$ aryl, ($C_6$-$C_{14}$) aryl-linear or branched alkyl ($C_1$-$C_5$);

$R_8$ and $R_9$, which may be the same or different is hydrogen, hydroxy, linear or branched $C_1$-$C_5$ alkoxy;

their $N_1$-oxides, their single isomers, in particular the syn and anti isomers of the —C($R_{11}$)═N—O$_{(n)}R_{10}$ group, their enantiomers, diastereoisomers and admixtures, the pharmaceutically acceptable salts thereof, the molar ratio between the compound of the formula (II) and the taxol or the camptothecin is 40:1.

8. The composition according to claim 7, in which X⁻ is selected from the group consisting of chloride; bromide; iodide; aspartate; citrate; tartrate; phosphate; fumarate; glycerophosphate; glucose phosphate; lactate; maleate; mucate; orotate; oxalate; sulphate; trichloroacetate; trifluoroacetate; methane sulphonate; and pamoate.

9. The composition according to claim 7, in which the compound of formula (II) is selected from the group consisting of palmitoyl L-carnitine chloride undecyl ester; and stearoyl L-carnitine chloride undecyl ester.

10. The composition according to claim 7, in which the liposome additionally contains helper lipids.

11. The composition according to claim 10, in which said helper lipid is selected from the group consisting of cholesterol, 1-palmitoyl-2-oleoyl phosphatidyl choline or dioleyl phosphatidyl choline.

12. The composition according to claim 7, in which the composition is administered orally, parenterally, intravenously, intramuscularly, subcutaneously, transdermally or in the form of a nasal mouth spray.

13. A method of transporting an antitumor drug to the target organ of a subject in need of antitumor treatment, wherein said drug is selected from the group consisting of taxol or a camptothecin derivative of formula

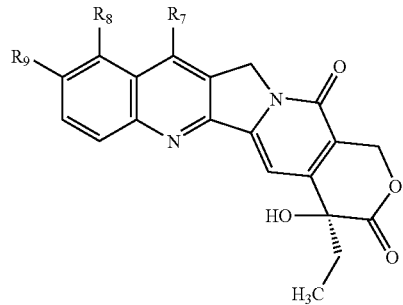

wherein: $R_7$ is a —C($R_{11}$)═N—O$_{(n)}R_{10}$ group, wherein $R_{10}$ is hydrogen or a $C_1$-$C_5$ alkyl or $C_2$-$C_5$ alkenyl group, linear or branched or $C_3$-$C_{10}$ cycloalkyl, group or a linear or branched ($C_3$-$C_{10}$) cycloalkyl-($C_1$-$C_5$) alkyl group, or $C_6$-$C_{14}$ aryl, or a linear or branched ($C_6$-$C_{14}$) aryl-($C_1$-$C_5$) alkyl group, or a heterocyclic or linear or branched heterocyclo-($C_1$-$C_5$) alkyl group, said heterocyclic group containing at least a heteroatom selected from the group consisting of nitrogen atom, optionally substituted with a ($C_1$-$C_5$) alkyl group, and/or oxygen and/or sulfur; said alkyl, alkenyl, cycloalkyl, cycloalkylalkyl, aryl, aryl-alkyl, heterocyclic or heterocyclo-alkyl groups, being optionally substituted with other groups selected from the group consisting of: halogen, hydroxy, $C_1$-$C_5$ alkyl, $C_1$-$C_5$ alkoxy, phenyl, cyano, nitro, —NR$_{12}$R$_{13}$, wherein $R_{12}$ and $R_{13}$, which may be the same or different, are hydrogen, linear or branched ($C_1$-$C_5$) alkyl; a pharmaceutically acceptable ester of the —COOH group; or the —CONR$_{14}$R$_{15}$ group, wherein $R_{14}$ and $R_{15}$, which may be the same or different, are hydrogen or linear or branched ($C_1$-$C_5$) alkyl; or $R_{10}$ is a ($C_6$-$C_{10}$) aroyl residue optionally substituted by one or more groups selected from the group consisting of: halogen, hydroxy, linear or branched ($C_1$-$C_5$) alkyl, $C_1$-$C_5$ alkoxy, phenyl, cyano, nitro, —$NR_{16}R_{17}$, wherein $R_{16}$ and $R_{17}$, which may be the same or different, are hydrogen, linear or branched ($C_1$-$C_8$) alkyl;

n is the number 0 or 1;

$R_{11}$ is hydrogen, linear or branched $C_1$-$C_5$ alkyl, linear or branched $C_2$-$C_5$ alkenyl, $C_3$-$C_{10}$ cycloalkyl, ($C_3$-$C_{10}$) cycloalkyl-linear or branched ($C_1$-$C_5$) alkyl, $C_6$-$C_{14}$ aryl, ($C_6$-$C_{14}$) aryl-linear or branched alkyl ($C_1$-$C_5$);

$R_8$ and $R_9$, which may be the same or different are hydrogen, hydroxy, linear or branched $C_1$-$C_5$ alkoxy;

their $N_1$-oxides, their single isomers, in particular the syn and anti isomers of the —$C(R_{11})$=N—$O_{(n)}R_{10}$ group, their enantiomers, diastereoisomers and admixtures, the pharmaceutically acceptable salts thereof;

said method comprising encapsulating said antitumor drug into a liposome comprising a compound of formula (II)

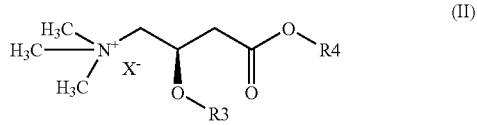

(II)

where:

$R_3$ is an acyl chain selected from the group consisting of palmitoyl and stearoyl;

$R_4$ is undecyl; the molar ratio between the compound of the formula (II) and the taxol or the camptothecin is 40:1; and $X^-$ is the anion of a pharmacologically acceptable acid, to obtain a liposome containing said antitumor drug, and administering said liposome to said subject.

14. The method according to claim 13, in which X— is selected from the group consisting of chloride; bromide; iodide; aspartate; citrate; tartrate; phosphate; fumarate; glycerophosphate; glucose phosphate; lactate; maleate; mucate; orotate; oxalate; sulphate; trichloroacetate; trifluoroacetate; methane sulphonate; and pamoate.

15. The method according to claim 13, in which the compound of formula (II) is selected from the group consisting of palmitoyl L-carnitine chloride undecyl ester; and stearoyl L-carnitine chloride undecyl ester.

16. The method according to claim 13, in which said derivative of camptothecin is selected from the group consisting of 7-benzyloxyiminomethylcamptothecin or 7-t-butoxyiminomethyl camptothecin.

17. The method according to claim 13, in which the liposome additionally contains helper lipids.

18. The method according to claim 17, in which said helper lipid is selected from the group consisting of cholesterol, 1-palmitoyl-2-oleoyl phosphatidyl choline or dioleyl phosphatidyl choline.

19. The method according to claim 13, wherein said antitumor drug is 7-t-butoxyiminomethylcamptothecin and said liposome comprises the compound palmitoyl L-carnitine undecyl ester.

20. The method according to claim 13, wherein said antitumor drug is taxol and said liposome comprises the compound palmitoyl L-carnitine undecyl ester.

21. The method according to claim 13, wherein said liposome is administered orally, parenterally, intravenously, intramuscularly, subcutaneously, transdermally or in the form of a nasal or mouth spray.

22. The method according to claim 13, wherein lungs are said target organ.

23. The method according to claim 1, wherein said liposome is in the form of a dry powder.

24. The method according to claim 1, wherein said liposome is adsorbed on an inert support.

25. The method according to claim 24, wherein the inert support is selected from the group consisting of sorbitol, trehalose and mannitol.

26. The composition according to claim 7, wherein said liposome is in the form of a dry powder.

27. The method according to claim 7, wherein said liposome is adsorbed on an inert support.

28. The method according to claim 27, wherein the inert support is selected from the group consisting of sorbitol, trehalose, lactose and mannitol.

29. The method according to claim 13, wherein said liposome is in the form of a dry powder.

30. The method according to claim 13, wherein said liposome is adsorbed on an inert support.

31. The method according to claim 30, wherein the inert support is selected from the group consisting of sorbitol, trehalose and mannitol.

32. A method of transporting an antitumor drug to the lungs of a subject in need of antitumor treatment, wherein said drug is selected from the group consisting of taxol or a camptothecin derivative of formula

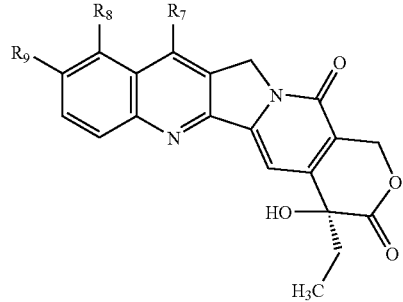

wherein: $R_7$ is a —$C(R_{11})$=N—$O_{(n)}R_{10}$ group, wherein $R_{10}$ is hydrogen or a $C_1$-$C_5$ alkyl or $C_2$-$C_5$ alkenyl group, linear or branched or G3-$C_{10}$ cycloalkyl, group or a linear or branched ($C_3$-$C_{10}$) cycloalkyl-($C_1$-$C_5$) alkyl group, or $C_6$-$C_{14}$ aryl, or a linear or branched ($C_6$-$C_{14}$) aryl-($C_1$-$C_5$) alkyl group, or a heterocyclic or linear or branched heterocyclo-($C_1$-$C_5$) alkyl group, said heterocyclic group containing at least a heteroatom selected from the group consisting of nitrogen atom, optionally substituted with a ($C_1$-$C_5$) alkyl group, and/or oxygen and/or sulfur; said alkyl, alkenyl, cycloalkyl, cycloalkylalkyl, aryl, aryl-alkyl, heterocyclic or heterocyclo-alkyl groups, being optionally substituted with other groups selected from the group consisting of: halogen, hydroxy, $C_1$-$C_5$ alkyl, $C_1$-$C_5$ alkoxy, phenyl, cyano, nitro, —$NR_{12}R_{13}$, wherein $R_{12}$ and $R_{13}$, which may be the same or different, are hydrogen, linear or branched ($C_1$-$C_5$) alkyl; a pharmaceutically acceptable ester of the —COOH group; or the —$CONR_{14}R_{15}$ group, wherein $R_{14}$ and $R_{15}$, which may be the same or different, are hydrogen or linear or branched ($C_1$-$C_5$) alkyl; or $R_{10}$ is a ($C_6$-$C_{10}$) aroyl residue optionally substituted by one or more groups selected from the group consisting of: halogen, hydroxy, linear or branched ($C_1$-$C_5$) alkyl, $C_1$-$C_5$ alkoxy, phenyl, cyano, nitro, —$NR_{16}R_{17}$, wherein $R_{16}$ and $R_{17}$, which may be the same or different, are hydrogen, linear or branched ($C_1$-$C_8$) alkyl;

n is the number 0 or 1;

$R_{11}$ is hydrogen, linear or branched $C_1$-$C_5$ alkyl, linear or branched $C_2$-$C_5$ alkenyl, $C_3$-$C_{10}$ cycloalkyl, ($C_3$-$C_{10}$) cycloalkyl-linear or branched ($C_1$-$C_5$) alkyl, $C_6$-$C_{14}$ aryl, ($C_6$-$C_{14}$) aryl-linear or branched alkyl ($C_1$-$C_5$);

$R_8$ and $R_9$, which may be the same or different are hydrogen, hydroxy, linear or branched $C_1$-$C_5$ alkoxy;

their $N_1$-oxides, their single isomers, in particular the syn and anti isomers of the —C($R_{11}$)=N—O$_{(n)}$R$_{10}$ group, their enantiomers, diastereoisomers and admixtures, the pharmaceutically acceptable salts thereof;

said method comprising encapsulating said antitumor drug into a liposome comprising a compound of formula (II)

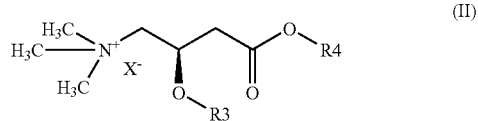

where:

$R_3$ is an acyl chain selected from the group consisting of palmitoyl and stearoyl;

$R_4$ is undecyl; the molar ratio between the compound of the formula (II) and the taxol or the camptothecin is 40:1; and $X^-$ is the anion of a pharmacologically acceptable acid, to obtain a liposome containing said antitumor drug, and administering said liposome to said subject.

33. The method according to claim 32, in which $X^-$ is selected from the group consisting of chloride; bromide; iodide; aspartate; citrate; tartrate; phosphate; fumarate; glycerophosphate; glucose phosphate; lactate; maleate; mucate; orotate; oxalate; sulphate; trichloroacetate; trifluoroacetate; methane sulphonate; and pamoate.

34. The method according to claim 32, in which the compound of formula (II) is selected from the group consisting of palmitoyl L-carnitine chloride undecyl ester; and stearoyl L-carnitine chloride undecyl ester.

35. The method according to claim 32, in which said derivative of camptothecin is selected from the group consisting of 7-benzyloxyiminomethylcamptothecin or 7-t-butoxyiminomethylcamptothecin.

36. The method according to claim 32, in which the liposome additionally contains helper lipids.

37. The method according to claim 36, in which said helper lipid is selected from the group consisting of cholesterol, 1-palmitoyl-2-oleoyl phosphatidyl choline or dioleyl phosphatidyl choline.

38. The method according to claim 32, wherein said antitumor drug is 7-t-butoxyiminomethylcamptothecin and said liposome comprises the compound palmitoyl L-carnitine undecyl ester.

39. The method according to claim 32, wherein said antitumor drug is taxol and said liposome comprises the compound palmitoyl L-carnitine undecyl ester.

40. The method according to claim 32, wherein said liposome is administered orally, parenterally, intravenously, intramuscularly, subcutaneously, transdermally or in the form of a nasal or mouth spray.

41. A method of intracellular delivery of an antitumor drug into tumor cells to the lungs of a subject in need of antitumor treatment, wherein said drug is selected from the group consisting of taxol or a camptothecin derivative of formula

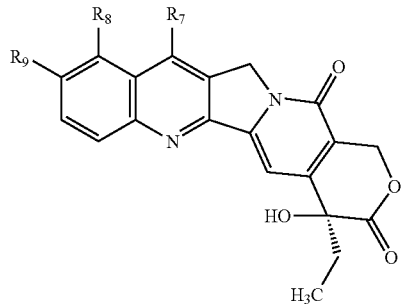

wherein: $R_7$ is a —C($R_{11}$)=N—O$_{(n)}$R$_{10}$ group, wherein $R_{10}$ is hydrogen or a $C_1$-$C_5$ alkyl or $C_2$-$C_5$ alkenyl group, linear or branched or $C_3$-$C_{10}$ cycloalkyl, group or a linear or branched ($C_3$-$C_{10}$) cycloalkyl-($C_1$-$C_5$) alkyl group, or $C_6$-$C_{14}$ aryl, or a linear or branched ($C_6$-$C_{14}$) aryl-($C_1$-$C_5$) alkyl group, or a heterocyclic or linear or branched heterocyclo-($C_1$-$C_5$) alkyl group, said heterocyclic group containing at least a heteroatom selected from the group consisting of nitrogen atom, optionally substituted with a ($C_1$-$C_5$) alkyl group, and/or oxygen and/or sulfur; said alkyl, alkenyl, cycloalkyl, cycloalkylalkyl, aryl, aryl-alkyl, heterocyclic or heterocyclo-alkyl groups, being optionally substituted with other groups selected from the group consisting of: halogen, hydroxy, $C_1$-$C_5$ alkyl, $C_1$-$C_5$ alkoxy, phenyl, cyano, nitro, —NR$_{12}$R$_{13}$, wherein $R_{12}$ and $R_{13}$, which may be the same or different, are hydrogen, linear or branched ($C_1$-$C_5$) alkyl; a pharmaceutically acceptable ester of the —COOH group; or the —CONR$_{14}$R$_{15}$ group, wherein $R_{14}$ and $R_{15}$, which may be the same or different, are hydrogen or linear or branched ($C_1$-$C_5$) alkyl; or $R_{10}$ is a ($C_6$-$C_{10}$) aroyl residue optionally substituted by one or more groups selected from the group consisting of: halogen, hydroxy, linear or branched ($C_1$-$C_5$) alkyl, $C_1$-$C_5$ alkoxy, phenyl, cyano, nitro, —NR$_{16}$R$_{17}$, wherein $R_{16}$ and $R_{17}$, which may be the same or different, are hydrogen, linear or branched ($C_1$-$C_8$) alkyl;

n is the number 0 or 1;

$R_{11}$ is hydrogen, linear or branched $C_1$-$C_5$ alkyl, linear or branched $C_2$-$C_5$ alkenyl, $C_3$-$C_{10}$ cycloalkyl, ($C_3$-$C_{10}$) cycloalkyl-linear or branched ($C_1$-$C_5$) alkyl, $C_6$-$C_{14}$ aryl, ($C_6$-$C_{14}$) aryl-linear or branched alkyl ($C_1$-$C_5$);

$R_8$ and $R_9$, which may be the same or different are hydrogen, hydroxy, linear or branched $C_1$-$C_5$ alkoxy;

their $N_1$-oxides, their single isomers, in particular the syn and anti isomers of the —C($R_{11}$)N—O$_{(n)}$R$_{10}$ group, their enantiomers, diastereoisomers and admixtures, the pharmaceutically acceptable salts thereof;

said method comprising encapsulating said antitumor drug into a liposome comprising a compound of formula (II)

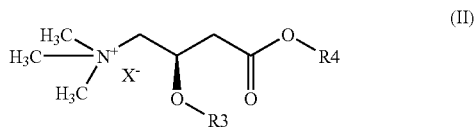

where:
i. $R_3$ is palmitoyl and $R_4$ is undecyl; or
ii. $R_3$ is stearoyl and $R_4$ is undecyl;
the molar ratio between the compound of the formula (II) and the taxol or the camptothecin is 40:1; and
$X^-$ is the anion of a pharmacologically acceptable acid, to obtain a liposome containing said antitumor drug,
and
administering said liposome to said subject.

42. The method according to claim 41, in which $X^-$ is selected from the group consisting of chloride; bromide; iodide; aspartate; citrate; tartrate; phosphate; fumarate; glycerophosphate; glucose phosphate; lactate; maleate; mucate; orotate; oxalate; sulphate; trichloroacetate; trifluoroacetate; methane sulphonate; and pamoate.

43. The method according to claim 41, in which said derivative of camptothecin is selected from the group consisting of 7-benzyloxyiminomethylcamptothecin or 7-t-butoxyiminomethylcamptothecin.

44. The method according to claim 41, in which the liposome additionally contains helper lipids.

45. The method according to claim 44, in which said helper lipid is selected from the group consisting of cholesterol, 1-palmitoyl-2-oleoyl phosphatidyl choline or dioleyl phosphatidyl choline.

46. The method according to claim 41, wherein said antitumor drug is 7-t-butoxyiminomethylcamptothecin and said liposome comprises the compound palmitoyl L-carnitine undecyl ester.

47. The method according to claim 41, wherein said antitumor drug is taxol and said liposome comprises the compound palmitoyl L-carnitine undecyl ester.

48. The method according to claim 41, wherein said liposome is administered orally, parenterally, intravenously, intramuscularly, subcutaneously, transdermally or in the form of a nasal or mouth spray.

* * * * *